US007541003B2

(12) United States Patent
Pohl et al.

(10) Patent No.: US 7,541,003 B2
(45) **Date of Patent: *Jun. 2, 2009**

(54) LATEX BASED ADSORBENT CHIP

(75) Inventors: Christopher A. Pohl, Union City, CA (US); Steven C. Papanu, Palo Alto, CA (US)

(73) Assignee: Bio-Rad Laboratories, Inc., Hercules, CA (US)

(*) Notice: Subject to any disclaimer, the term of this patent is extended or adjusted under 35 U.S.C. 154(b) by 227 days.

This patent is subject to a terminal disclaimer.

(21) Appl. No.: 10/197,115

(22) Filed: Jul. 16, 2002

(65) Prior Publication Data

US 2003/0032043 A1 Feb. 13, 2003

Related U.S. Application Data

(63) Continuation-in-part of application No. 09/908,518, filed on Jul. 17, 2001.

(60) Provisional application No. 60/383,008, filed on May 23, 2002.

(51) Int. Cl.
*B01D 15/10* (2006.01)
*G01N 30/00* (2006.01)

(52) U.S. Cl. .......................... 422/69; 435/174; 210/656

(58) Field of Classification Search ..................... 435/4, 435/7.1, 287.7, 287.8; 436/518, 527, 532; 521/25, 28
See application file for complete search history.

(56) References Cited

U.S. PATENT DOCUMENTS 3,951,893 A * 4/1976 Gander ....................... 524/322
5,719,060 A * 2/1998 Hutchens et al. ............ 436/174
6,225,047 B1 * 5/2001 Hutchens et al. ............... 435/5
6,251,691 B1 * 6/2001 Seul ........................... 436/534
6,329,209 B1 * 12/2001 Wagner et al. ............. 436/518

OTHER PUBLICATIONS

Du et al., "Two-Dimensional Arrays from Polymer Spheres in Nanoscale Prepared by the Langmuir-Blodgett Method", Apr. 30, 1997, Langmuir, vol. 13, No. 9, pp. 2538-2540.*
Aizenberg et al., "Patterned Colloidal Deposition Controlled by Electrostatic and Capillary Forces", Mar. 27, 2000, Physical Review Letters, Vol. 84, Issue 13, pp. 2997-3000.*
Sigma Sepharose-Based ion Exchange Media Product Information Sheet Downloaded from www.sigmaaldrich.com Jul. 5, 2007.*
Ikeda et al (1983 Makromol. Chem. Rapid Commun. 4:459-461).*
Ferreira et al (2000 Biotech Prog. 16:416-424).*

* cited by examiner

*Primary Examiner*—Christopher Low
*Assistant Examiner*—Christopher M. Gross
(74) *Attorney, Agent, or Firm*—Morgan, Lewis & Bockius LLP

(57) ABSTRACT

The present invention provides an adsorbent chip, which includes three components, a substrate, an intermediate layer of linker arms and an adsorbent film, which is attached to the linker arms. The adsorbent film is made up of a plurality of adsorbent particles, each of which includes a binding functionality. The invention also provides a method of making the chips of the invention in which the substrate-intermediate film cassette is formed and the adsorbent film is subsequently immobilized thereon. When the adsorbent film is from the same preparation across a particular batch of chips, the chips provide for the acquisition of data that are highly reproducible from one chip to the next throughout the particular batch of chips. Additionally, the invention provides methods for using the chips to perform assays.

19 Claims, 10 Drawing Sheets

Step-3: Attach Latex Electrostatically

Anion Exchange Functional Groups

N,N - Dimethylethanolamine

SAX-L1

N,N - Dimethyloctylamine

SAX-L2

N-methylglucamine

WAX

Cation Exchange Functional Groups

3-Mercaptopropionate

WCX

3-Mercaptopropanesulfonate

SCX

N,N - Bis(carboxymethyl)-L-Lysine

IMAC

Monomer used to Couple Silane to the glass surface

Methacryloxypropyltrimethoxysilane (MAOPTMS)

Functionalize glass surfaces with this monomer in the presence of MeOH, water, and acid Step-1: Silane Coupling to the Glass Surface Step-2: Grafting the Appropriate Monomers Acrylic Acid N-(3-N',N'-dimethylaminopropyl) methacrylamide Step-3: Attach Latex Electrostatically Reaction to Produce Anion Exchange Groups Anion exchange group

Reaction to Produce Cation Exchange Groups

LATEX BASED ADSORBENT CHIP

CROSS-REFERENCES TO RELATED APPLICATIONS

This application is a non-provisional of application Ser. No. 09/908,518 filed Jul. 17, 2001, and claims the benefit of provisional Application No. 60/383,008 filed May 23, 2002, the disclosures of which are incorporated herein by reference for all purposes.

BACKGROUND OF THE INVENTION

Bioassays are used to probe for the presence and/or the quantity of a target material in a biological sample. In surface based assays, the target amount is quantified by capturing it on a solid support and then detecting it. One example of a surface-based assay is a DNA microarray. The use of DNA microarrays has become widely adopted in the study of gene expression and genotyping due to the ability to monitor large numbers of genes simultaneously (Schena et al., *Science* 270: 467-470 (1995); Pollack et al., *Nat. Genet.* 23:41-46 (1999)). More than 100,000 different probe sequences can be bound to distinct spatial locations across the microarray surface, each spot corresponding to a single gene (Schena et al., *Tibtech* 16:301-306 (1998)). When a fluorescent-labeled DNA target sample is placed over the surface of the array, individual DNA strands hybridize to complementary strands within each array spot. The level of fluorescence detected quantifies the number of copies bound to the array surface and therefore the relative presence of each gene, while the location of each spot determines the gene identity. Using arrays, it is theoretically possible to simultaneously monitor the expression of all genes in the human genome. This is an extremely powerful technique, with applications spanning all areas of genetics (For some examples, see the Chipping Forecast supplement to *Nature Genetics* 21 (1999)). Arrays can also be fabricated using other binding moieties such as antibodies, proteins, haptens or aptamers, in order to facilitate a wide variety of bioassays in array format.

Other surface-based assays include microtitre plate-based ELISAs in which the bottom of each well is coated with a different antibody. A protein sample is then added to each well along with a fluorescent-labeled secondary antibody for each protein. Target proteins are captured on the surface of each well and secondarily labeled with a fluorophore. The fluorescence intensity at the bottom of each well is used to quantify the amount of each target molecule in the sample. Similarly, antibodies or DNA can be bound to a microsphere such as a polymer bead and assayed as described above. Once again, each of these assay formats is amenable for use with a plurality of binding moieties as described for arrays.

Other bioassays are of use in the fields of proteomics, and the like. For example, cell function, both normal and pathologic, depends, in part, on the genes expressed by the cell (i.e., gene function). Gene expression has both qualitative and quantitative aspects. That is, cells may differ both in terms of the particular genes expressed and in terms of the relative level of expression of the same gene. Differential gene expression is manifested, for example, by differences in the expression of proteins encoded by the gene, or in post-translational modifications of expressed proteins. For example, proteins can be decorated with carbohydrates or phosphate groups, or they can be processed through peptide cleavage. Thus, at the biochemical level, a cell represents a complex mixture of organic biomolecules.

One goal of functional genomics ("proteomics") is the identification and characterization of organic biomolecules that are differentially expressed between cell types. By comparing expression, one can identify molecules that may be responsible for a particular pathologic activity of a cell. For example, identifying a protein that is expressed in cancer cells but not in normal cells is useful for diagnosis and, ultimately, for drug discovery and treatment of the pathology. Upon completion of the Human Genome Project, all the human genes will have been cloned, sequenced and organized in databases. In this "post-genome" world, the ability to identify differentially expressed proteins will lead, in turn, to the identification of the genes that encode them. Thus, the power of genetics can be brought to bear on problems of cell function.

Differential chemical analyses of gene expression and function require tools that can resolve the complex mixture of molecules in a cell, quantify them and identify them, even when present in trace amounts. The current tools of analytical chemistry for this purpose are presently limited in each of these areas. One popular biomolecular separation method is gel electrophoresis. Frequently, a first separation of proteins by isoelectric focusing in a gel is coupled with a second separation by sodium dodecyl sulfate-polyacrylamide gel electrophoresis (SDS-PAGE). The result is a map that resolves proteins according to the dimensions of isoelectric point (net charge) and size (i.e., mass). Although useful, this method is limited in several ways. First, the method provides information only about two characteristics of a biomolecule-mass and isoelectric point ("pI"). Second, the resolution power in each of the dimensions is limited by the resolving power of the gel. For example, molecules whose mass differ by less than about 5% or less than about 0.5 pI are often difficult to resolve. Third, gels have limited loading capacity, and thus limited sensitivity; one often cannot detect biomolecules that are expressed in small quantities. Fourth, small proteins and peptides with a molecular mass below about 10-20 kDa are not observed.

The use of functionalized chips is replacing gels as the method of choice for bioassays. Efforts to improved the sensitivity of assays have resulted in a number of chip designs. For example, a specific binding assay device, which comprises multilayer analytical materials is known (see, for example, EP 51183, EP 66648, DE 3227474 and EP 236768). other multilayer chips are set forth in U.S. Pat. Nos. 4,839,278 and 4,356,149.

An effective chip for bioassay applications must have adequate capacity to immobilize a sufficient amount of an analyte from relevant samples in order to provide a suitable signal when subjected to detection (e.g., mass spectroscopy analysis). Suitable chips must also provide a highly reproducible surface in order to be gainfully applied to profiling experiments, particularly in assay formats in which the sample and the control must be analyzed on separate adjacent chip surfaces. Chips that are not based on a highly reproducible surface chemistry result in significant errors when undertaking assays (e.g., profiling comparisons).

In general, currently available chips are based on in-situ polymerization of a hydrogel on each spot of a bioassay chip (see, e.g., WO 00/66265 (Rich et al.) The selectivity and reproducibility of these chips is highly dependent upon a large number of experimental variables including, monomer concentration, monomer ratios, initiator concentration, solvent evaporation rate, ambient humidity (in the case when the solvent is water), crosslinker concentration, laboratory temperature, pipetting time, sparging conditions, reaction temperature (in the case of thermal polymerizations), reaction humidity, uniformity of ultraviolet radiation (in the case of UV photopolymerization) and ambient oxygen conditions. While many of these parameters can be controlled in a manufacturing setting, is difficult if not impossible to control all of these parameters which impinge upon reproducibility. As a result, in situ polymerizations results in relatively poor reproducibility of all parameters including spot to spot, chip to chip and lot to lot.

Thus, there is a tremendous need for chips that provide reproducible results from assay to assay, are easy to use, and provide quantitative data in multi-analyte systems. Moreover, to become widely accepted, the chips should be inexpensive to make, and to use for the detection of analytes. The availability of a chip having the above-described characteristics would significantly affect research, individual point of care situations (doctor's office, emergency room, out in the field, etc.), and high throughput testing applications. The present invention provides chips having these and other desirable characteristics

BRIEF SUMMARY OF THE INVENTION

It has now been discovered that a solution to the shortcomings of prior chips resides in the synthesis of an adsorbent film in a process that is separate from the process by which the film is attached to the substrate of the chip. By separating the attachment of the film from the synthesis of the adsorbent particles making up the film, the individual processes are more readily controlled. Furthermore, if sufficient adsorbent material is synthesized using a material of suitable chemical stability, one can readily synthesize enough material to allow the use of a single lot of stationary phase over the entire product lifecycle of a given chip of the invention. Quite surprisingly, in an embodiment of the methods set forth herein, approximately one million chips of the invention can be prepared from less than four liters of adsorbent material. Thus, using this present method one can produce chips with minimal variability in selectivity over the entire product lifecycle.

The devices of the present invention function as adsorbent biochips that comprise three parts: a substrate that functions to support the adsorbent film attached to its surface; an intermediate layer that is attached to the substrate surface and that comprises linker arms through which the adsorbent film is attached to the substrate; and the adsorbent film that comprises adsorbent particles that will immobilize analytes on the chip.

The nature of the substrate depends upon the intended use of the adsorbent biochip. If the chip is to be used in linear time-of-flight mass spectrometry, the substrate preferably includes a conductive material, such as a metal. If the biochip is to be used in mass spectrometry involving orthogonal extraction, the substrate preferably includes a non-conductive material. If the biochip is to be used in another detection method, such as fluorescence detection at the biochip surface, suitable materials, such as plastics or glass can be used. The substrate typically will have functional groups through which the intermediate layer can be attached. For example, an aluminum chip can be covered with silicon dioxide. Other metals, such as anodized aluminum already have surfaces with functional groups. Alternatively, the substrate may be composed of plastic in which case the functional groups may already be present as an integral surface component or the surface may be derivatized, making use of methods well-known to those skilled in the art.

The intermediate layer includes linker arms. In preferred embodiments the intermediate layer is attached to the substrate at discrete locations, addressable according to location and addressable by interrogation means, such as light directed at a spot. The use of the intermediate layer allows one to attach a pre-synthesized adsorbent material to the substrate, rather than constructing the adsorbent material directly on the substrate. The attachment is preferably accomplished through an initial electrostatic interaction, e.g., the intermediate layer comprises linker arms having a charge and the adsorbent particles have the opposite charge.

In certain embodiments, the initial electrostatic attraction between the linkers and the particles is augmented or replaced by a second binding mechanism. In an exemplary embodiment, the second binding mechanism is selected from physisorption, chemisorption, polymer entanglement, or a combination thereof. Other second binding mechanisms include, but are not limited to, hydrophobic-hydrophobic, hydrophilic-hydrophilic, dipole-dipole, van der Waals, covalent bonding, ionic bonding and the like.

The second binding mechanism provides an attraction between the intermediate layer and the adsorbent particles that is surprisingly stable over a wide range of conditions. It has been found that, in one embodiment, the invention provides chips, which are stable at pHs that would be expected to cause dissociation of the particles from linkers to which they were bound by simple electrostatic attraction. For example, positively charged particles immobilized on negatively charged linkers do not dissociate upon a decrease in the pH, which would be sufficient to protonate the negatively charged linkers (e.g., COO— to COOH).

Linker arms of the intermediate layer can be attached directly or indirectly to the substrate. In a preferred embodiment, the intermediate layer is formed by attaching an anchor moiety to the substrate surface and forming the linker arms by a polymerization process initiated at a functional group of the anchor moiety. The linker arms and the adsorbent material are subsequently coupled.

In one embodiment the substrate includes reactive groups, such as hydroxyls. The anchoring moiety can be a silicon-derivative comprising a reactive group that can function as a locus for polymerization initiation. While a vinyl group is preferred for polymerization process, any functional group can be used on which the polymers can be built. A preferred material for anchoring is 3-(trimethoxysilyl)propylmethacrylate.

In those embodiments of the invention in which an electrostatic interaction between oppositely charged linkers and particles is exploited, the linker arms preferably include at least one moiety that is positively or negatively charged. In an exemplary embodiment, the linker arm includes at least one charged moiety derived from a positively or negatively charged monomer (any polymerizable monomer with a charged functional group or a protected charged functional group is useful). A preferred negatively charged monomer is acrylic acid. A preferred positively charged monomer is N-(3-N,N-dimethylaminopropyl)methacrylamide. Furthermore, the polymer formed from the monomers can be a homopolymer, or a heteropolymer.

The adsorbent layer is formed from adsorbent particles comprising a binding functionality. The adsorbent particles are preferably applied to the intermediate layer in the form of a colloidal suspension. Prior to being functionalized, the particles preferably have diameters between about 10 nm and about 100 μm. Small diameter particles are typically between about 400 nm to about 500 nm in diameter. Large diameter particles are typically between about 1 μm and about 100 μm, more preferably between about 1 μm and about 50 μm.

Functionalization of the particles typically leads to a dramatic increase in their size. Thus, small functionalized particles are typically from about 3 μ to about 10 μ in diameter. Functionalized large diameter particles are generally from about 10 μ to about 500 μ in diameter.

Normally, the functionalized particles will carry a charge opposite to the charge of the linker arms, thereby facilitating electrostatic attraction between the intermediate layer and the particles, leading to the attachment of these two components. The preferred suspensions of this invention are based on a derivatized polyvinylbenzyl chloride. This is one of the most well characterized latexes and, therefore, straightforward to work with. One also can use other substitutable styrenic monomers for polymerization.

In an exemplary embodiment using adsorbent particles formed from vinylbenzyl chloride, the beads are functionalized by substituting the chloride with a desired functionality. In certain embodiments, the functionalities can be positively charged (anion exchange), negatively charged (cation exchange), a chelating agent, e.g., that can engage in coordiate covalent bonding with a metal ion or a biospecific compound, e.g., an antibody or cellular receptor. Preferred compounds for derivatization include N,N-dimethylethanolamine (strong anion exchange or "SAX"), N,N-dimethyloctylamine (SAX), N-methylglucamine (weak anion exchange or "WAX"), 3-mercaptopropane sulfonate (strong cation exchange or "SCX"), 3-mercaptopropionate (weak cation exchange or "WCX") or N,N-bis(carboxymethyl)-L-lysine (immobilized metal chelate or "IMAC").

In another aspect, this invention provides a method for detecting an analyte in a sample comprising contacting the analyte with an adsorbent biochip of this invention to allow capture of the analyte and detecting capture of the analyte by the adsorbent chip. In certain embodiments, the analyte is a biomolecule, such as a polypeptide, a polynucleotide, a carbohydrate or a lipid. In other embodiments, the analyte is an organic molecule such as a drug candidate. In certain embodiments, the analyte is detected by mass spectrometry, in particular by laser desorption/ionization mass spectrometry. In such methods, when the analyte is a biomolecule, the method preferably comprises applying a matrix to the captured analyte before detection. In other embodiments the analyte is labeled, e.g., fluorescently, and is detected on the chip by a detector of the label, e.g., a fluorescence detector such as a CCD array. In certain embodiments the method involves profiling a certain class of analytes (e.g., biomolecules) in a sample by applying the sample to one or addressable locations and detecting analytes captured at the addressable location or locations.

In another aspect, this invention provides a method for making an adsorbent chip. The method includes: a) covalently coupling an anchor reagent to a substrate surface via complementary reactive groups on the surface and the anchor reagent, wherein the anchor reagent comprises a locus for polymerization; b) polymerizing a plurality of polymerizable monomers to the anchor reagent through the locus, whereby a brush polymer is formed; and c) contacting the brush polymer with a plurality of adsorbent particles comprising binding functionalities, thereby forming an adsorbent film immobilized on the brush polymer.

In another aspect, this invention provides a method for making a plurality of adsorbent chips. The method includes: (a) providing a plurality of chip precursors, each chip precursor comprising a substrate having a surface and an intermediate layer attached to the surface, wherein the intermediate layer comprises linker arms having a charge; and (b) contacting each of the intermediate layers with an aliquot comprising adsorbent particles having a charge opposite to the charge of the linker arms, wherein the adsorbent particles comprise binding functionalities, whereby the adsorbent particles are attached to the intermediate layer, and wherein the aliquots come from a single batch of adsorbent particles. In one embodiment, the intermediate layers are attached to each substrate surface at a plurality of addressable locations on the surface. In another embodiment the batch has a volume between 0.5 liters and 5 liters. In another embodiment, the total area of the addressable locations made from the batch is at least 500,000 $mm^2$. In another embodiment the total area of the addressable locations made from the batch is between 500,000 $mm^2$ and 50,000,000 $mm^2$. In another embodiment the number of addressable locations is between 100,000 and 5 million.

Other aspects, objects and advantages of the present invention will be apparent from the detailed description that follows.

DETAILED DESCRIPTION OF THE INVENTION AND THE PREFERRED EMBODIMENTS

Definitions

Figure 1:
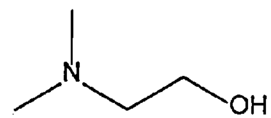
FIG. 1 is a collection of structures of representative anion exchange (positively charged) binding moieties of use in preparing the chips of the invention.
Figure 1:
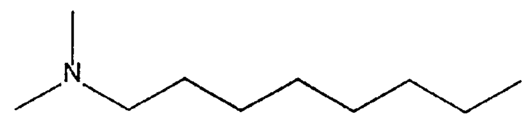
Figure 1:
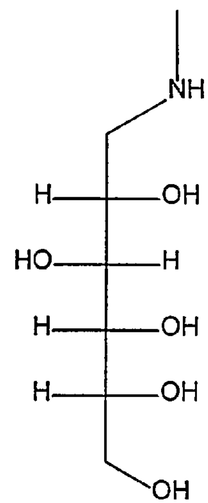

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization described below are those well known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

As used herein, "nucleic acid" means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, points of attachment and functionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications such as capping with a fluorophore (e.g., quantum dot) or another moiety.

"Peptide" refers to a polymer in which the monomers are amino acids and are joined together through amide bonds, alternatively referred to as a "polypeptide." Unnatural amino acids, for example, β-alanine, phenylglycine and homoarginine are also included under this definition. Amino acids that are not gene-encoded may also be used in the present invention. Furthermore, amino acids that have been modified to include reactive groups may also be used in the invention. All of the amino acids used in the present invention may be either the D- or L-isomer. The L-isomers are generally preferred. In addition, other peptidomimetics are also useful in the present invention. For a general review, see, Spatola, A. F., in CHEMISTRY AND BIOCHEMISTRY OF AMINO ACIDS, PEPTIDES AND PROTEINS, B. Weinstein, eds., Marcel Dekker, N.Y., p. 267 (1983).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid.

"Antibody" refers to a polypeptide ligand substantially encoded by an immunoglobulin gene or immunoglobulin genes, or fragments thereof, which specifically binds and recognizes an epitope (e.g., an antigen). The recognized immunoglobulin genes include the kappa and lambda light chain constant region genes, the alpha, gamma, delta, epsilon and mu heavy chain constant region genes, and the myriad immunoglobulin variable region genes. Antibodies exist, e.g., as intact immunoglobulins or as a number of well characterized fragments produced by digestion with various peptidases. This includes, e.g., Fab' and $F(ab)'_2$ fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies, humanized antibodies, or single chain antibodies. The "Fc" portion of an antibody refers to that portion of an immunoglobulin heavy chain that comprises one or more heavy chain constant region domains, CH1, CH2 and CH3, but does not include the heavy chain variable region.

As used herein, an "immunoconjugate" means any molecule or ligand such as an antibody or growth factor (i.e., hormone) chemically or biologically linked to a fluorophore, a cytotoxin, an anti-tumor drug, a therapeutic agent or the like. Examples of immunoconjugates include immunotoxins and antibody conjugates.

Where substituent groups are specified by their conventional chemical formulae, written from left to right, they equally encompass the chemically identical substituents which would result from writing the structure from right to left, e.g., $—CH_2O—$ is intended to also recite $—OCH_2—$; $—NHS(O)_2—$ is also intended to represent. $—S(O)_2HN—$, etc.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups, which are limited to hydrocarbon groups are termed "homoalkyl".

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, $—CH_2—CH_2—O—CH_3$, $—CH_2—CH_2—NH—CH_3$, $—CH_2—CH_2—N(CH_3)—CH_3$, $—CH_2—S—CH_2—CH_3$, $—CH_2—CH_2$, $—S(O)—CH_3$, $—CH_2—CH_2—S(O)_2—CH_3$, $—CH{=}CH—O—CH_3$, $—Si(CH_3)_3$, $—CH_2—CH{=}N—OCH_3$, and $—CH{=}CH—N(CH_3)—CH_3$. Up to two heteroatoms may be consecutive, such as, for example, $—CH_2—NH—OCH_3$ and $—CH_2—O—Si(CH_3)_3$. Similarly, the term "heteroalkylene"

by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', ═O, ═NR', ═N—OR', —NR'R", —SR', -halogen, —SiR'R"R"', —OC(O)R', —C(O)R', —$CO_2$R', —CONR'R", —OC(O)NR'R", —NR"C(O)R', —NR'—C(O)NR"R"', —NR"C(O)$_2$R', —NR—C(NR'R"R"')═NR"", —NR—C(NR'R")═NR"', —S(O)R', —S(O)$_2$R', —S(O)$_2$NR'R", —$NRSO_2$R', —CN and —$NO_2$ in a number ranging from zero to (2m'+1), where m' is the total number of carbon atoms in such radical. R', R", R"' and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R"' and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Each of the above terms are meant to include both substituted and unsubstituted forms of the indicated radical.

As used herein, the term "heteroatom" is meant to include oxygen (O), nitrogen (N), sulfur (S) and silicon (Si).

"Target," and "target species, as utilized herein refers to the species of interest in an assay mixture. Exemplary targets include, but are not limited to cells and portions thereof, enzymes, antibodies and other biomolecules, drugs, pesticides, herbicides, agents of war and other bioactive agents.

The term "substance to be assayed" as used herein means a substance, which is detected qualitatively or quantitatively by the process or the device of the present invention. Examples of such substances include antibodies, antibody fragments, antigens, polypeptides, glycoproteins, polysaccharides, complex glycolipids, nucleic acids, effector molecules, receptor molecules, enzymes, inhibitors and the like.

More illustratively, such substances include, but are not limited to, tumor markers such as α-fetoprotein, carcinoembryonic antigen (CEA), CA 125, CA 19-9 and the like; various proteins, glycoproteins and complex glycolipids such as $\beta_2$-microglobulin ($\beta_2$ m), ferritin and the like; various hormones such as estradiol ($E_2$), estriol ($E_3$), human chorionic gonadotropin (hCG), luteinizing hormone (LH), human placental lactogen (hPL) and the like; various virus-related antigens and virus-related antibody molecules such as HBs antigen, anti-HBs antibody, HBc antigen, anti-HBc antibody, anti-HCV antibody, anti-HIV antibody and the like; various allergens and their corresponding IgE antibody molecules; narcotic drugs and medical drugs and metabolic products thereof; and nucleic acids having virus- and tumor-related polynucleotide sequences.

The term, "assay mixture," refers to a mixture that includes the target and other components. The other components are, for example, diluents, buffers, detergents, and contaminating species, debris and the like that are found mixed with the target. Illustrative examples include urine, sera, blood plasma, total blood, saliva, tear fluid, cerebrospinal fluid, secretory fluids from nipples and the like. Also included are solid, gel or sol substances such as mucus, body tissues, cells and the like suspended or dissolved in liquid materials such as buffers, extractants, solvents and the like.

The term "drug" or "pharmaceutical agent," refers to bioactive compounds that cause an effect in a biological organism. Drugs used as affinity moieties or targets can be neutral or in their salt forms. Moreover, the compounds can be used in the present method in a prodrug form. Prodrugs are those compounds that readily undergo chemical changes under physiological conditions to provide the compounds of interest in the present invention.

The term "binding functionality" as used herein means a moiety, which has an affinity for a certain substance such as a "substance to be assayed," that is, a moiety capable of interacting with a specific substance to immobilize it on the chip of the invention. Binding functionalities can be chromatographic or biospecific. Chromatographic binding functionalities bind substances via charge-charge, hydrophilic-hydrophilic, hydrophobic-hydrophobic, van der Waals interactions and combinations thereof. Biospecific binding functionalities generally involve complementary 3-dimensional structures involving one or more of the above interactions. Examples of combinations of biospecific interactions include, but are not limited to, antigens with corresponding antibody molecules, a nucleic acid sequence with its complementary sequence, effector molecules with receptor molecules, enzymes with inhibitors, sugar chain-containing compounds with lectins, an antibody molecule with another antibody molecule specific for the former-antibody, receptor molecules with corresponding antibody molecules and the like combinations. Other examples of the specific binding substances include a chemically biotin-modified antibody molecule or polynucleotide with avidin, an avidin-bound antibody molecule with biotin and the like combinations.

The term "adsorbent film" as used herein means an area where a substance to be assayed is immobilized and a specific binding reaction occurs having a distribution along the flow direction of a test sample.

As used herein, the terms "polymer" and "polymers" include "copolymer" and "copolymers," and are used interchangeably with the terms "oligomer" and "oligomers."

The term "detection means" as used herein refers to detecting a signal produced by the immobilization of the substance to be assayed onto the binding layer by visual judgment or by using an appropriate external measuring instrument depending on the signal properties.

The term "attached," as used herein encompasses interaction including, but not limited to, covalent bonding, ionic bonding, chemisorption, physisorption and combinations thereof.

The term "independently selected" is used herein to indicate that the groups so described can be identical or different.

The term "biomolecule" or "bioorganic molecule" refers to an organic molecule typically made by living organisms. This includes, for example, molecules comprising nucleotides, amino acids, sugars, fatty acids, steroids, nucleic acids, polypeptides, peptides, peptide fragments, carbohydrates, lipids, and combinations of these (e.g., glycoproteins, ribonucleoproteins, lipoproteins, or the like).

The term "biological material" refers to any material derived from an organism, organ, tissue, cell or virus. This includes biological fluids such as saliva, blood, urine, lymphatic fluid, prostatic or seminal fluid, milk, etc., as well as extracts of any of these, e.g., cell extracts, cell culture media, fractionated samples, or the like.

Introduction

The present invention provides a chip that is readily assembled from a substrate; an adsorbent film, which includes a binding functionality; and an intermediate layer of linker arms connecting the two aforementioned components. The invention disclosed herein also includes methods using a chip of the invention for increasing the sensitivity, specificity and dynamic range of assay systems based upon the capture of a target species with the binding functionality. The assays are surface based; a component of the assay (e.g., the binding functionality) is bound to a substrate through the intermediate layer.

The present invention is further explained and illustrated in the sections which follow, by reference to a representative embodiment using detection by mass spectrometry. The focus on mass spectrometric detection is for purposes of clarity and simplicity of illustration only, and should not be construed as limiting the scope of the present invention or circumscribing the types of methods in which the present invention finds application. Those of skill in the art will recognize that the methods set forth herein are broadly applicable to a number of chip formats and assays using these chips for the detection of a wide range of target moieties.

The Chip

In an exemplary embodiment, the chips of the invention include: (1) a substrate; (2) an intermediate layer, which includes linker arms and is attached to the substrate; and (3) an adsorbent film whose components include a binding functionality. Preferably, the intermediate layer further comprises an anchor moiety that is bound to the substrate, and serves as the point of attachment to the substrate for a charged polymer that forms the linker arm. The adsorbent film components generally have a net charge that is opposite that of the charged polymer/linker arm, such that the polymer and the film components are attracted each to the other. The electrostatic attraction between the film components and the charged polymer anchors the film component to the intermediate layer and, thus, to the substrate. The binding functionality, whose function is to immobilize the analyte to the adsorbent film, is a moiety of substantially any useful structure for a particular application.

The components of the chip of the invention are discussed in detail hereinbelow. Those of skill will appreciate that each of the described preferred and alternate embodiments of each of the components are readily combined with the embodiments of other components without limitation.

The Substrate

In the chip of the invention, the adsorbent film is immobilized on a substrate, either directly or through linker arm arms of the intermediate layer that are intercalated between the substrate and the adsorbent film. The intermediate layer comprising the linker arms is bound to the plane of the substrate surface, or it is bound to a feature of the substrate surface which may be flush with the surface, raised (e.g., island) or depressed (e.g., a well, trough, etc.). Substrates that are useful in practicing the present invention can be made of any stable material, or combination of materials. Moreover, useful substrates can be configured to have any convenient geometry or combination of structural features. The substrates can be either rigid or flexible and can be either optically transparent or optically opaque. The substrates can also be electrical insulators, conductors or semiconductors. When the sample to be applied to the chip is water based, the substrate preferable is water insoluble.

The materials forming the substrate are utilized in a variety of physical forms such as films, supported powders, glasses, crystals and the like. For example, a substrate can consist of a single inorganic oxide or a composite of more than one inorganic oxide. When more than one component is used to form a substrate, the components can be assembled in, for example a layered structure (i.e., a second oxide deposited on a first oxide) or two or more components can be arranged in a contiguous non-layered structure. Further the substrates can be substantially impermeable to liquids, vapors and/or gases or, alternatively, the substrates can be permeable to one or more of these classes of materials. Moreover, one or more components can be admixed as particles of various sizes and deposited on a support, such as a glass, quartz or metal sheet. Further, a layer of one or more components can be intercalated between two other substrate layers (e.g., metal-oxide-metal, metal-oxide-crystal). Those of skill in the art are able to select an appropriately configured substrate, manufactured from an appropriate material for a particular application.

Exemplary substrate materials include, but are not limited to, inorganic crystals, inorganic glasses, inorganic oxides, metals, organic polymers and combinations thereof. Inorganic glasses and crystals of use in the substrate include, but are not limited to, LiF, NaF, NaCl, KBr, KI, $CaF_2$, $MgF_2$, $HgF_2$, BN, $AsS_3$, ZnS, $Si_3N_4$, AlN and the like. The crystals and glasses can be prepared by art standard techniques. See, for example, Goodman, Crystal Growth Theory and Techniques, Plenum Press, New York 1974. Alternatively, the crystals can be purchased commercially (e.g., Fischer Scientific). Inorganic oxides of use in the present invention include, but are not limited to, $Cs_2O$, $Mg(OH)_2$, $TiO_2$, $ZrO_2$, $CeO_2$, $Y_2O_3$, $Cr_2O_3$, $Fe_2O_3$, NiO, ZnO, $Al_2O_3$, $SiO_2$ (glass), quartz, $In_2O_3$, $SnO_2$, $PbO_2$ and the like. Metals of use in the substrates of the invention include, but are not limited to, gold, silver, platinum, palladium, nickel, copper and alloys and composites of these metals.

Metals are also of use as substrates in the present invention. The metal can be used as a crystal, a sheet or a powder. In those embodiments in which the metal is layered with another substrate component, the metal can be deposited onto the other substrate by any method known to those of skill in the art including, but not limited to, evaporative deposition, sputtering and electroless deposition.

The metal layers can be either permeable or impermeable to materials such as liquids, solutions, vapors and gases. Presently preferred metals include, but are not limited to, gold, silver, platinum, palladium, nickel, aluminum, copper, stainless steel, and other iron alloys.

Organic polymers that form useful substrates include, for example, polyalkenes (e.g., polyethylene, polyisobutene, polybutadiene), polyacrylics (e.g., polyacrylate, polymethyl methacrylate, polycyanoacrylate), polyvinyls (e.g., polyvinyl alcohol, polyvinyl acetate, polyvinyl butyral, polyvinyl chloride), polystyrenes, polycarbonates, polyesters, polyurethanes, polyamides, polyimides, polysulfone, polysiloxanes, polyheterocycles, cellulose derivative (e.g., methyl cellulose, cellulose acetate, nitrocellulose), polysilanes, fluorinated polymers, epoxies, polyethers and phenolic resins.

In a preferred embodiment, the substrate material is substantially non-reactive with the target, thus preventing non-specific binding between the substrate and the target or other components of an assay mixture. Methods of coating substrates with materials to prevent non-specific binding are generally known in the art. Exemplary coating agents include, but are not limited to cellulose, bovine serum albumin, and poly(ethyleneglycol). The proper coating agent for a particular application will be apparent to one of skill in the art.

In a further preferred embodiment, the substrate material is substantially non-fluorescent or emits light of a wavelength range that does not interfere with the detection of the target. Exemplary low-background substrates include those disclosed by Cassin et al., U.S. Pat. No. 5,910,287 and Pham et al., U.S. Pat. No. 6,063,338.

The surface of a substrate of use in practicing the present invention can be smooth, rough and/or patterned. The surface can be engineered by the use of mechanical and/or chemical techniques. For example, the surface can be roughened or patterned by rubbing, etching, grooving, stretching, and the oblique deposition of metal films. The substrate can be patterned using techniques such as photolithography (Kleinfield et al., *J. Neurosci.* 8: 4098-120 (1998)), photoetching, chemical etching and microcontact printing (Kumar et al., *Langmuir* 10: 1498-511 (1994)). Other techniques for forming patterns on a substrate will be readily apparent to those of skill in the art.

The size and complexity of the pattern on the substrate is limited only by the resolution of the technique utilized and the purpose for which the pattern is intended. For example, using microcontact printing, features as small as 200 nm have been layered onto a substrate. See, Xia, Y.; Whitesides, G., *J. Am. Chem. Soc.* 117:3274-75 (1995). Similarly, using photolithography, patterns with features as small as 1 μm have been produced. See, Hickman et al., *J. Vac. Sci. Technol.* 12:607-16 (1994). Patterns that are useful in the present invention include those which comprise features such as wells, enclosures, partitions, recesses, inlets, outlets, channels, troughs, diffraction gratings and the like.

In an exemplary embodiment, the patterning is used to produce a substrate having a plurality of adjacent addressable features, wherein each of the features is separately identifiable by a detection means. In another exemplary embodiment, an addressable feature does not fluidically communicate with other adjacent features. Thus, an analyte, or other substance, placed in a particular feature remains substantially confined to that feature. In another preferred embodiment, the patterning allows the creation of channels through the device whereby fluids can enter and/or exit the device.

In those embodiments in which the anchor moiety, the linker arm, the adsorbent film or combinations thereof are printed onto the substrate, the pattern can be printed directly onto the substrate or, alternatively, a "lift off" technique can be utilized. In the lift off technique, a patterned resist is laid onto the substrate, component of the chip is laid down in those areas not covered by the resist and the resist is subsequently removed. Resists are known to those of skill in the art. See, for example, Kleinfield et al., *J. Neurosci.* 8:4098-120 (1998). In some embodiments, following removal of the resist, a second chip component, having a structure different from the first component layer is printed onto the substrate on those areas initially covered by the resist; a process that can be repeated any selected number of times with different components to produce a chip having a desired format.

Using the technique set forth above, substrates with patterns having regions of different chemical characteristics can be produced. Thus, for example, a pattern having an array of adjacent isolated features is created by varying the hydrophobicity/hydrophilicity, charge and other chemical characteristics of the pattern constituents. For example, hydrophilic compounds can be confined to individual hydrophilic features by patterning "walls" between the adjacent features using hydrophobic materials. Similarly, positively or negatively charged compounds can be confined to features having "walls" made of compounds with charges similar to those of the confined compounds. Similar substrate configurations are also accessible through microprinting a layer with the desired characteristics directly onto the substrate. See, Mrkish, M.; Whitesides, G. M., *Ann. Rev. Biophys. Biomol. Struct.* 25:55-78 (1996).

The specificity and multiplexing capacity of the chips of the invention can be increased by incorporating spatial encoding (e.g., spotted microarrays) into the chip substrate. Spatial encoding can be introduced into each of the chips of the invention. In an exemplary embodiment, binding functionalities for different analytes can be arrayed across the chip surface, allowing specific data codes (e.g., target-binding functionality specificity) to be reused in each location. In this case, the array location is an additional encoding parameter, allowing the detection of a virtually unlimited number of different analytes.

In the embodiments of the invention in which spatial encoding is utilized, they preferably utilize a spatially encoded array comprising m binding functionalities distributed over m regions of the substrate. Each of the m binding functionalities can be a different functionality or the same functionality, or different functionalities can be arranged in patterns on the surface. For example, in the case of matrix array of addressable locations, all the locations in a single row or column can have the same binding functionality. The m binding functionalities are preferably patterned on the substrate in a manner that allows the identity of each of the m locations to be ascertained. In a preferred embodiment, the m binding functionalities are ordered in a p by q matrix of (p×q) discrete locations, wherein each of the (p×q) locations has bound thereto at least one of the m binding functionalities. The microarray can be patterned from essentially any type of binding functionality.

The spatially encoded assay substrates can include essentially any number of compounds. In an embodiment in which the binding functionalities are polynucleotides (oligonucleotides or nucleic acids) or polypeptides, m is a number from 1 to 100, more preferably, from 10 to 1,000, and more preferably from 100 to 10,000.

In a particularly preferred embodiment, the substrate includes an aluminum support that is coated with a layer of silicon dioxide. In yet a further preferred embodiment, the silicon dioxide layer is from about 1000-3000 Å in thickness.

Those of skill in the art will appreciate that the above-described and other methods are useful for preparing arrays of a wide variety of compounds in addition to nucleic acids, are useful for preparing arrays of a wide variety of compounds in addition to nucleic acids.

The Intermediate Layer

Attached to the substrate and linking the adsorbent film to the substrate is the intermediate layer. The intermediate layer is made of a population of individual linker arms. The members may behave as isolated individuals, or they may cooperate to form an ordered structure such as a self-assembled monolayer. Alternatively, the layer can be cross-linked to impart stability or other desirable characteristics to the chip.

The members of the population of linker arms are of any useful structure. Preferred linkers are those derived from a species with a reactive functional group complementary to a reactive group on the substrate and a second functional group that interacts with the adsorbent film to adhere it to the linker arm film.

In an exemplary embodiment, the intermediate layer is a two-component structure comprising an "anchor moiety," which is attached to the substrate, and the linker arms which couple to a member of the adsorbent film.

Anchor Moiety

A number of reaction types are available for the functionalization of a substrate surface with an anchor moiety. For example, substrates constructed of a plastic such as polypropylene, can be surface derivatized by chromic acid oxidation, and subsequently converted to hydroxylated or aminomethylated surfaces. Substrates made from highly crosslinked divinylbenzene can be surface derivatized by chloromethylation and subsequent functional group manipulation. Additionally, functionalized substrates can be made from etched, reduced poly-tetrafluoroethylene. Other methods of derivatizing polymeric substrates are known to those of skill in the art.

In an exemplary embodiment the substrate is made of glass, or of metal that is coated with a glass-like material and, thus, presents a surface with reactive Si—OH bonds. When the anchor moiety is attached to glass, the anchor moiety will generally include a first functional group of reactivity complementary to the bonds at the surface of the glass.

A number of siloxane functionalizing reagents can be used to form the anchor moiety. Exemplary reagents include, but are not limited to:

1. hydroxyalkyl siloxanes (Silylate surface, functionalize with diborane, and $H_2O_2$ to oxidize the alcohol)
   a. allyl trichlorosilane→→3-hydroxypropyl,
   b. 7-oct-1-enyl trichlorchlorosilane→→8-hydroxyoctyl;
2. diol(dihydroxyalkyl) siloxanes (silylate surface and hydrolyze to diol)
   a. (glycidyl trimethoxysilane→→(2,3-dihydroxypropyloxy)propyl;
3. aminoalkyl siloxanes (amines requiring no intermediate functionalizing step)
   a. 3-aminopropyl trimethoxysilane→aminopropyl;
4. dimeric secondary aminoalkyl siloxanes
   a. bis(3-trimethoxysilylpropyl)amine→bis(silyloxylpropyl)amine; and
5. unsaturated species (e.g., acryloyl, methacryloyl, styryl, etc.).

In a still further exemplary embodiment, the anchor moiety is derived from a species having the structure:

$$(RO)_3\text{—Si—}R^1\text{—}X^1 \quad (1)$$

in which R is an alkyl group, e.g., methyl or ethyl, $R^1$ is a linking group between silicon and $X^1$, and $X^1$ is a reactive group or a protected reactive group. The reactive group can also be a member of the adsorbent layer as discussed below. Silane derivatives having halogens or other leaving groups beside the displayed alkoxy groups are also useful in the present invention.

In a presently preferred embodiment, the anchor moiety is derived from a member selected from group 4, above. Preferred anchor moieties are those, for example, that are derived from styrylethyltrimethoxysilane, styrylethylmethyldimethoxysilane, styrylethyldimethylmethoxysilane, styrylethyltrichlorosilane, styrylethylmethyldimethoxysilane, styrylethyldimethylmethoxysilane, (3-acryloxypropyl)trimethoxysilane, (3-acryloxypropyl)methyldimethoxysilane, (3-acryloxypropyl)dimethylmethoxysilane, (3-acryloxypropyl)trichlorosilane, (3-acryloxypropyl)methyldichlorosilane, (3-acryloxypropyl)dimethylchlorosilane, (3-methacryloxypropyl)trimethoxysilane, (3-methacryloxypropyl)methyldimethoxysilane, (3-methacryloxypropyl)dimethylmethoxysilane, (3-methacryloxypropyl)trichlorosilane, (3-methacryloxypropyl)methyldichlorosilane, (3-methacryloxypropyl)dimethylchlorosilane and combinations thereof.

In another exemplary embodiment, the substrate is at least partially a metal film, e.g., a gold film, and the reactive group is tethered to the metal surface by an agent displaying avidity for that surface. In a presently preferred embodiment, the substrate is at least partially a gold film and the group, which reacts with the metal surface includes a thiol, sulfide or disulfide such as:

$$Y\text{—S—}R^2\text{—}X^2 \quad (2)$$

in which $R^2$ is a linking group between sulfur and $X^2$, and $X^2$ is a reactive group or a protected reactive group. $X^2$ can also be a member of the adsorbent film. Y is a member selected from the group consisting of H, $R^3$ and $R^3$—S—, wherein $R^3$ is H or alkyl.

A large number of functionalized thiols, sulfides and disulfides are commercially available (Aldrich Chemical Co., St. Louis). Additionally, those of skill in the art have available to them a manifold of synthetic routes with which to produce additional such molecules. For example, amine-functionalized thiols can be produced from the corresponding haloamines, halo-carboxylic acids, etc. by reaction of these halo precursors with sodium sulfhydride. See, for example, Reid, Organic Chemistry of Bivalent Sulfur, vol. 1, pp. 21-29, 32-35, vol. 5, pp. 27-34, Chemical Publishing Co., New York, 1958, 1963. Additionally, functionalized sulfides can be prepared via alkylthio-dehalogenation with a mercaptan salt. See, Reid, Organic Chemistry of Bivalent Sulfur, vol. 2, pp. 16-21, 24-29, vol. 3, pp. 11-14, Chemical Publishing Co., New York, 1960. Other methods for producing compounds useful in practicing the present invention will be apparent to those of skill in the art.

In another preferred embodiment, the anchor moiety provides for more than one reactive group per each anchor moiety. Using a reagent such as that shown below, each reactive site on the substrate surface, which is bound to an anchor moiety, is "amplified" into two or more reactive groups.

$$(RO)_3\text{—Si—}R^1\text{—}(X^1)_n \quad (3)$$

In Formula 3, R is an alkyl group, such as methyl, $R^1$ is a linking group between silicon and $X^1$, $X^1$ is a reactive group or a protected reactive group and n is an integer between 2 and 50, and more preferably between 2 and 20. In a preferred embodiment, (—Si—$R^1$—) is methacryloxypropylsilane.

Similar amplifying molecules are also of use in those embodiments wherein the substrate is at least partially a metal film. In these embodiments the group, which reacts with the metal surface comprises a thiol, sulfide or disulfide such as in Formula 4:

$$Y\text{—S—}R^2\text{—}(X^2)_n \quad (4)$$

in which the symbols $R^2$, $X^2$, Y, $R^3$ have substantially the same meanings discussed above.

Exemplary groups of use for $R^1$, $R^2$ and $R^3$ in the above described embodiments of the present invention include, but are not limited to, alkyl, substituted alkyl, aryl, arylalkyl, substituted aryl, substituted arylalkyl, acyl, alkylamino, acylamino, alkoxy, acyloxy, aryloxy, aryloxyalkyl, saturated cyclic hydrocarbon, unsaturated cyclic hydrocarbon, heteroaryl, heteroarylalkyl, substituted heteroaryl, substituted heteroarylalkyl, heterocyclic, substituted heterocyclic and heterocyclicalkyl groups In each of Formulae 1-4, above, each of $R^1$, $R^2$ and $R^3$ are either stable or they can be cleaved, e.g., by chemical or photochemical reactions. For example, an anchor moiety that includes an ester or disulfide bond can be cleaved by hydrolysis and reduction, respectively. Upon cleavage, the adsorbent film is released from the substrate. Also within the scope of the present invention is the use of groups, which are cleaved by light such as, for example, nitrobenzyl derivatives, phenacyl groups, benzoin esters, etc. Other such cleaveable groups are well known to those of skill in the art. Many cleaveable groups are known in the art. See, for example, Jung et al., *Biochem. Biophys. Acta,* 761: 152-162 (1983); Joshi et al., *J. Biol. Chem.,* 265: 14518-14525 (1990); Zarling et al., *J. Immunol.,* 124: 913-920 (1980); Bouizar et al., *Eur. J. Biochem.,* 155: 141-147 (1986); Park et al., *J. Biol. Chem.,* 261: 205-210 (1986); Browning et al., *J. Immunol.,* 143: 1859-1867 (1989).

Reactive Functional Groups

Reactive functional groups are included within a number of components of the chips of the invention. For example, a reactive functional group on the anchor moiety reacts with an incoming subunit used to build the linker arm and to tether the linker arms to the substrate. Moreover, the binding functionality can include a reactive functional group. The reactive functional groups discussed herein are generally applicable at any site of the chip in which a coupling reaction or recognition event occurs.

Exemplary reactive functional groups (e.g., $X^1$ and $X^2$) include:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups, which can be converted to esters, ethers, aldehydes, etc.;

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups, which are capable of participating in Diels-Alder reactions such as, for example, maleimido groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides or reacted with acyl halides;

(h) amine or sulfhydryl groups, which can be, for example, acylated or alkylated;

(i) alkenes, which can undergo, for example, cycloadditions, acylation, Michael addition, etc; and (j) epoxides, which can react with, for example, amines and hydroxyl compounds.

The reactive functional groups can be chosen such that they do not participate in, or interfere with reactions in which they are not intended to participate. Alternatively, the reactive functional group can be protected from participating in the reaction by the presence of a protecting group. Those of skill in the art will understand how to protect a particular functional group from interfering with a chosen set of reaction conditions. For examples of useful protecting groups, See Greene et al., PROTECTIVE GROUPS IN ORGANIC SYNTHESIS, John Wiley & Sons, New York, 1991.

Those of skill in the art will understand that the reactive functional groups discussed herein represent only a subset of functional groups that are useful in assembling the chips of the invention. Moreover, those of skill will understand that the reactive functional groups are also of use as components of the adsorbent film and the linker arms.

In a particularly preferred embodiment, the reactive functional group includes an unsaturated carbon-carbon or carbon-heteroatom bond. In a still further preferred embodiment, the reactive functional group includes at least one vinyl group, which is suitable for radical polymerization.

Linker Arms

The layer of linker arms, also referred to herein as "the support," or "film support," immobilizes the adsorbent film. The layer of linker arms is of any composition and configuration useful to immobilize the adsorbent film. The linker arms are bound to the second functional group of the anchor moiety (i.e., the one not bound directly to the substrate), thereby becoming immobilized on the substrate. The linker arms also have one or more groups that interact with the adsorbent film. In a preferred embodiment, the linker arm is a charged moiety, having a charge that is opposite in sign from that of the components of the adsorbent film.

The linker arms are preferably selected from organic and biological polymers, although small molecule linkers (e.g., biotin) are also encompassed within the scope of the present invention. A fully assembled linker can be coupled to the anchor moiety. Alternatively, the linker arms can be assembled on the substrate-anchor conjugate by coupling together monomers using a functional group on the anchor moiety as the origin of polymer synthesis. In yet another exemplary embodiment, the support-anchor moiety is formed as a cassette, which is subsequently attached to the substrate. The linker arm preferably is attached to only one anchor moiety. The point of attachment preferably is at an end of the linker arm, but could be an internal attachment. The linker arm can be a linear molecular strand or can be branched. Preferably, the linker arms on a substrate are not crosslinked with one another. In a preferred embodiment, the collection of linker arms forms a "brush polymer," that is, a collection of molecular strands, each independently attached to the substrate.

Exemplary synthetic linker species useful in the chips of the present invention include both organic and inorganic polymers and may be formed from any compound, which will support the immobilization of the adsorbent film. For example, synthetic polymer ion-exchange resins such as poly (phenol-formaldehyde), polyacrylic, or polymethacrylic acid or nitrile, amine-epichlorohydrin copolymers, graft polymers of styrene on polyethylene or polypropylene, poly(2-chloromethyl-1,3-butadiene), poly(vinylaromatic) resins such as those derived from styrene, $\alpha$-methylstyrene, chlorostyrene, chloromethylstyrene, vinyltoluene, vinylnaphthalene or vinylpyridine, corresponding esters of methacrylic acid, styrene, vinyltoluene, vinylnaphthalene, and similar unsaturated monomers, monovinylidene monomers including the monovinylidine ring-containing nitrogen heterocyclic compounds and copolymers of the above monomers are suitable.

The linker of the present invention can be formed by, for example, well-known suspension polymerization techniques, which involve suspending droplets of monomer in an aqueous medium in which it is insoluble. Under suitable conditions, the polymer will polymerize. This can be accomplished by mixing the monomer with additives in a suspension medium. When this medium is agitated, the monomer disperses into droplets and agitation continues until polymerization is complete.

In another embodiment, the linker is a lipophilic polymer. Exemplary lipophilic polymers are polyester (e.g., poly(lactide), poly(caprolactone), poly(glycolide), poly(δ-valerolactone), and copolymers containing two or more distinct repeating units found in these named polyesters), poly(ethylene-co-vinylacetate), poly(siloxane), poly(butyrolactone), and poly (urethane).

In a still further embodiment, the polymer is a hydrophilic polymer, for example, e.g., (a) a non-proteinaceous polymer selected from the group consisting of poly(ethylene oxide-co-propylene oxide), carboxylated poly(ethylene) (e.g., CARBOPOL™), poly(phosphazene), and polysaccharide; (b) a poly(amino acid); and (c) a blend of hydrophilic polymers. Other suitable hydrophilic polymers include polymers formed from ethylene oxide and propylene oxide polymers (including homopolymers and copolymers).

Other polymers of use in the present invention include cationic polymers, such as is exemplified by polyurethane compositions containing quaternary ammonium salts. The urethane polymers are readily prepared from alkylene oxides to prepare cationic polyurethane. See, for example, U.S. Pat. No. 3,470,310; U.S. Pat. No. 3,873,484.

Adsorbent Film

In the chips of the present invention, a class or type of molecular recognition event (e.g., adsorbent-target interaction) occurs at a binding functionality of an adsorbent film, thereby immobilizing a target on the film. The event is characterized by a particular selectivity condition, preferably occurring at an addressable location within the film.

In a preferred embodiment, the adsorbent film of the chips of the invention are configured such that detection of the immobilized analyte does not require elution, recovery, amplification, or labeling of the target analyte. Moreover, in another embodiment, the detection of one or more molecular recognition events, at one or more locations within the addressable adsorbent film, does not require removal or consumption of more than a small fraction of the total adsorbent-analyte complex. Thus, the unused portion can be interrogated further after one or more "secondary processing" events conducted directly in situ (i.e., within the boundary of the addressable location) for the purpose of structure and function elucidation, including further assembly or disassembly, modification, or amplification (directly or indirectly).

Adsorbents with improved specificity for an analyte can be developed by an iterative process, referred to as "progressive resolution," in which adsorbents or eluants proven to retain an analyte are tested with additional variables to identity combinations with better binding characteristics. Another method allows the rapid creation of substrates with antibody adsorbents specific for an analyte. The method involves docking the analyte to an adsorbent, and screening phage display libraries for phage that bind the analyte.

The adsorbent film is attached to the linker arm layer by one of many interaction modalities with which one of skill in the art is familiar. Representative modalities include, but are not limited to, covalent attachment, attachment via polymer entanglement and electrostatic attachment. In a preferred embodiment, the film is immobilized onto the film support by electrostatic attraction.

Unlike covalent attachment and polymer entanglement methodologies, electrostatic attachment is virtually instantaneous and film thickness is independent of attachment conditions. Covalent attachment and polymer entanglement methodologies suffer from many of the process control variables mentioned previously with respect to polymer synthesis. As a result, neither of these attachment methodologies can achieve uniformity in film thickness that approaches what is achievable using electrostatic attachment. In an exemplary embodiment, electrostatic attachment is as simple as depositing a slurry of charged particles onto an oppositely charged surface, and then rinsing excess particles off the surface. Film thickness is defined by the diameter of the particles. Electrostatic repulsions between coating particles preferably prevents multiple layers of particles becoming attached to the surface.

As discussed in the preceding section, the linker is preferably a multiply charged polymer. Thus, in a further preferred embodiment, the adsorbent layer is a polymeric material having a net charge that is the opposite of the net charge of the linker. A complex is formed between the two oppositely charged materials, thereby immobilizing the adsorbent film onto the intermediate layer.

The adsorbent layer of the chip of the invention is preferably a polymeric material and it can include biological polymers, synthetic polymers, hybrids of biological and synthetic polymers and combinations of these polymers. The only limitation on the structure of a polymer useful in the chips of the invention is that the polymer adhere to, bond to or be otherwise immobilized upon the intermediate layer.

The following discussion sets forth representative methods of preparing adsorbent particles of use in preparing the adsorbent films of the chips of the invention. The discussion is intended to be illustrative and does not define or limit the scope of particle types that are useful in the present invention.

In a preferred embodiment, the particles are used as a latex, or other aqueous particle dispersion. Exemplary latex particles are disclosed in U.S. Pat. Nos. 4,101,460; 4,252,644; 4,351,909; 4,383,047; 4,519,905; 4,927,539; 5,324,752; and 5,532,279. The term "latex" is used loosely herein to include classic latexes, comprising particles of a wide range of diameters.

The adsorbent layer is formed from adsorbent particles comprising a binding functionality. The adsorbent particles are preferably applied to the intermediate layer in the form of a colloidal suspension. Prior to being functionalized, the particles preferably have diameters between about 10 nm and about 100 μm. Small diameter particles are typically between about 400 nm to about 500 nm in diameter. Large diameter particles are typically between about 1 μm and about 100 μm, more preferably between about 1 μm and about 50 μm.

Functionalization of the particles typically leads to a dramatic increase in their size. For example, a functionalized particle, such as those described in the Examples, is typically from about 1 to about 2 orders of magnitude larger than the corresponding unfunctionalized particle. Thus, small functionalized particles are typically from about 3μ to about 10μ in diameter. Functionalized large diameter particles are generally from about 10μ to about 500 in diameter.

The diameter of the particles useful in the device and methods of the invention can be measured by any means known in the art for determining particle size. As used herein, "particle diameter," in reference to small particles, generally refers to an intensity weighted average as determined by photon correlation spectroscopy. More specifically, particle size was determined on particles suspended in aqueous 0.14% (by weight) tetra sodium pyrophosphate using a BI-90 (Brookhaven Instrument Corporation, Holtsville, N.Y.). Relevant to "large particles," diameter refers to a value that is generally determined by optical microscopy.

Examples of latex particles useful in practicing the present invention are set forth in the examples. Other representative methods of preparing latex particles are known in the art. For example, a process for the preparation of finely particulate plastics dispersions from a monomer mixture comprising various ethylenically unsaturated monomers, including 0.1 to 5% by weight of an α-, β-unsaturated monocarboxylic acid is disclosed in U.S. Pat. No. 4,193,902. The process involves metering the monomer mix simultaneously with an initiator into an aqueous liquor containing from 0.5 to 10% by weight of an anionic emulsifier, polymerizing the monomers to form the dispersion, and adjusting the dispersion to a pH of 7 to 10.

Dispersions of polymers comprising an olefinically unsaturated dicarboxylic acid or anhydride are disclosed in U.S. Pat. No. 5,356,968. The dispersions are obtained by emulsion polymerization of the monomers in the presence of an emulsifier mixture comprising at least two anionic emulsifiers and optionally one or more nonionic emulsifiers.

In DE-A-4026640, it is disclosed that oligomeric carboxylic acids can be used as stabilizers for the emulsion polymerization of olefinically unsaturated monomers and that this leads to fine particulate polymer dispersions that are coagulate-free and extremely shear stable.

Aqueous coating and lacquer compositions comprising a graft copolymer having carboxylic-acid functional moieties attached at a terminal end thereof to a polymeric backbone are described in WO-A-9532228 and WO-A-95322255.

Known anion-exchange compositions generally fall into several categories. In the more traditional anion-exchange systems, synthetic support resin particles, generally carrying a negative charge, are covered with a layer of smaller synthetic resin particles carrying anion-exchange functional groups of positive charge, i.e. anion-exchange sites. The smaller particles are retained on the larger support particles via electrostatic attraction. The support resin can take a variety of forms. See, for example U.S. Pat. Nos. 4,101,460; 4,383,047; 4,252,644; 4,351,909; and 4,101,460.

A more recent development utilizes an uncharged support resin and smaller latex particles containing anion-exchange functional groups, held together by a dispersant. See, U.S. Pat. No. 5,324,752.

Monomers used to form the particle components of the adsorbent film are preferably selected from the group consisting of methyl(meth)acrylate, ethyl(meth)acrylate, butyl (meth)acrylate, 2-ethylhexyl(meth)acrylate, decyl(meth) acrylate, lauryl(meth)acrylate, isobornyl(meth)acrylate, isodecyl(meth)acrylate, oleyl(meth)acrylate, palmityl(meth) acrylate, steryl(meth)acrylate, styrene, butadiene, vinyl acetate, vinyl chloride, vinylidene chloride, vinylbenzyl chloride, vinylbenzyl glycidyl ether, acrylonitrile, methacrylonitrile, acrylamide and glycidylmethacrylate, hydroxyethyl (meth)acrylate, hydroxypropyl(meth)acrylate, acrylic acid, methacrylic acid, crotonic acid, fumaric acid, maleic acid, mono-methyl itaconate, mono-methyl fumarate, monobutyl fumarate, maleic anhydride, substituted acrylamides, diacetone acrylamide, acetoacetoxy ethyl methacrylate, acrolein, methacrolein, dicyclopentadienyl methacrylate, dimethyl meta-isopropenyl benzyl isocyanate, isocyanato ethyl methacrylate, methyl cellulose, hydroxyethyl cellulose, ethylene, propylene, N-vinyl pyrrolidone, and N,N'-dimethylamino (meth)acrylate.

In certain embodiments, it is preferred to crosslink a percentage of the particle components of the adsorbent film. Any cross-linking agent, useful to crosslink the particles can be used to prepare the chips of the invention. In a preferred embodiment, the crosslinking agent is a polymerizable monomer. Preferred addition polymerizable crosslinking precursors include: ethylene glycol dimethacrylate (EGDMA); ethylene glycol diacrylate (EGDA); propylene glycol dimethacrylate; propylene glycol diacrylate; butylene glycol dimethacrylate; butylene glycol diacrylate; hexamethylene glycol dimethacrylate; hexamethylene glycol diacrylate; pentamethylene glycol diacrylate; pentamethylene glycol dimethacrylate; decamethylene glycol diacrylate; decamethylene glycol dimethacrylate; vinyl acrylate; divinyl benzene; glycerol triacrylate; trimethylolpropane triacrylate; pentaerythritol triacrylate; polyoxyethylated trimethylolpropane triacrylate and trimethacrylate and similar compounds as disclosed in U.S. Pat. No. 3,380,831; 2,2-di(p-hydroxyphenyl)-propane diacrylate; pentaerythritol tetraacrylate; 2,2-di-(p-hydroxyphenyl)-propane dimethacrylate; triethylene glycol diacrylate; polyoxyethyl-2,2-di-(p-hydroxyphenyl)-propane dimethacrylate; di-(3-methacryloxy-2-hydroxypropyl)ether of bisphenol-A; di-(2-methacryloxyethyl)ether of bisphenol-A; di-(3-acryloxy-2-hydroxypropyl)ether of bisphenol-A; di-(2-acryloxyethyl)ether of bisphenol-A; di-(3-methacryloxy-2-hydroxypropyl)ether of tetrachloro-bisphenol-A; di-(2-methacryloxyethyl)ether of tetrachloro-bisphenol-A; di-(3-methacryloxy-2-hydroxypropyl)ether of tetrabromo-bisphenol-A; di-(2-methacryloxyethyl)ether of tetrabromo-bisphenol-A; di-(3-methacryloxy-2-hydroxypropyl)ether of 1,4-butanediol; di-(3-methacryloxy-2-hydroxypropyl)ether of diphenolic acid; triethylene glycol dimethacrylate; polyoxypropyl one trimethylol propane triacrylate (462); 1,2,4-butanetriol trimethacrylate; 2,2,4-trimethyl-1,3-pentanediol dimethacrylate; pentaerythritol trimethacrylate; 1-phenyl ethylene-1,2-dimethacrylate; pentaerythritol tetramethacrylate; trimethylol propane trimethacrylate; 1,5-pentanediol dimethacrylate; diallyl fumarate; 1,4-benzenediol dimethacrylate; 1,4-diisopropenyl benzene; and 1,3,5-triisopropenyl benzene. A class of addition polymerizable crosslinking precursors are an alkylene or a polyalkylene glycol diacrylate or dimethacrylate prepared from an alkylene glycol of 2 to 15 carbons or a polyalkylene ether glycol of 1 to 10 ether linkages, and those disclosed in U.S. Pat. No. 2,927,022, e.g., those having a plurality of addition polymerizable ethylenic linkages particularly when present as terminal linkages. Members of this class are those wherein at least one and preferably most of such linkages are conjugated with a double bonded carbon, including carbon double bonded to carbon and to such heteroatoms as nitrogen, oxygen and sulfur. Also included are such materials wherein the ethylenically unsaturated groups, especially the vinylidene groups, are conjugated with ester or amide structures and the like.

Binding Functionality

For purposes of convenience, both the binding functionality and components of the binding functionality are referred to as the binding functionality.

Figure 2:
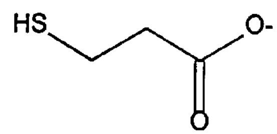
FIG. 2 is a collection of structures of representative cation exchange (negatively charged) binding moieties of use in preparing the chips of the invention.
Figure 2:
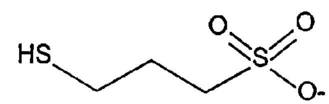
Figure 2:
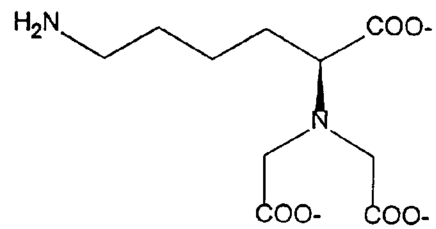
Figure 3:
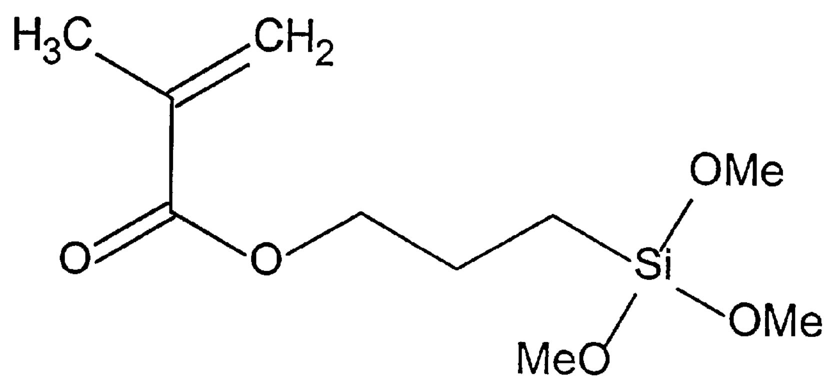
FIG. 3 is the structure of an exemplary silylating agent precursor of the anchor moiety

In an exemplary embodiment, the binding functionality comprises an organic functional group that interacts with a component of the target. In presently preferred embodiments, the organic functional group is selected from simple groups, such as amines (FIG. 1), carboxylic acids, sulfonic acids (FIG. 2), alcohols, sulfhydryls and the like. Functional groups presented by more complex species are also of use, such as those presented by drugs, chelating agents, crown ethers, cyclodextrins, and the like. In an exemplary embodiment, the binding functionality is an amine that interacts with a structure on the target that binds to the amine (e.g., carbonyl groups, alkylhalo groups), or which protonates the amine (e.g., carboxylic acid, sulfonic acid) to form an ion pair. In another exemplary embodiment, the binding functionality is a carboxylic acid, which interacts with the target by complexation (e.g., metal ions), or which protonate a basic group on the target (e.g. amine) forming an ion pair.

The organic functional group can be a component of a small organic molecule with the ability to specifically recognize a target molecule. Exemplary small organic molecules include, but are not limited to, amino acids, biotins, carbohydrates, glutathiones, and nucleic acids.

Exemplary amino acids suitable as binding functionaries, include L-alanine, L-arginine, L-asparagine, L-aspartic acid, L-cysteine, L-cystine, L-glutamic acid, L-glutamine, glycine, L-histidine, L-isoleucine, L-lysine, L-methionine, L-phenylalanine, L-proline, L-serine, L-threonine, L-thyroxine, D-tryptophan, L-tryptophan, L-tyrosine and L-valine. Typical avidin-biotin ligands include avidin, biotin, desthiobiotin, diaminobiotin, and 2-iminobiotin. Typical carbohydrates include glucoseamines, glycopryranoses, galactoseamines, the fucosamines, the fucopyranosylamines, the galactosylamines, the glycopyranosides, and the like. Typical glutathione ligands include glutathione, hexylglutathione, and sulfobromophthalein-S-glutathione.

In another exemplary embodiment, the binding functionality is a biomolecule, e.g., a natural or synthetic peptide, antibody, nucleic acid, saccharide, lectin, receptor, antigen, cell or a combination thereof. Thus, in an exemplary embodiment, the binding functionality is an antibody raised against a target or against a species that is structurally analogous to a target. In another exemplary embodiment, the binding functionality is avidin, or a derivative thereof, which binds to a biotinylated analogue of the target. In still another exemplary embodiment, the binding functionality is a nucleic acid, which binds to single- or double-stranded nucleic acid target having a sequence complementary to that of the binding functionality.

Biomolecules useful in practicing the present invention are derived from any source. The biomolecules can be isolated from natural sources or they can be produced by synthetic methods. Proteins can be natural proteins, mutated proteins or fusion proteins. Mutations can be effected by chemical mutagenesis, site-directed mutagenesis or other means of inducing mutations known to those of skill in the art. Proteins useful in practicing the instant invention include, for example, enzymes, antigens, antibodies and receptors. Antibodies can be either polyclonal or monoclonal.

Binding functionalities, which are antibodies can be used to recognize targets which include, but are not limited to, proteins, peptides, nucleic acids, saccharides or small molecules such as drugs, herbicides, pesticides, industrial chemicals, organisms, cells and agents of war. Methods of raising antibodies against specific molecules or organisms are well-known to those of skill in the art. See, U.S. Pat. No. 5,147,786, issued to Feng et al. on Sep. 15, 1992; U.S. Pat. No. 5,334,528, issued to Stanker et al. on Aug. 2, 1994; U.S. Pat. No. 5,686,237, issued to Al-Bayati, M. A. S. on Nov. 11, 1997; and U.S. Pat. No. 5,573,922, issued to Hoess et al. on Nov. 12, 1996.

Antibodies and other peptides can be attached to the adsorbent film by any known method. For example, peptides can be attached through an amine, carboxyl, sulfhydryl, or hydroxyl group. The site of attachment can reside at a peptide terminus or at a site internal to the peptide chain. The peptide chains can be further derivatized at one or more sites to allow for the attachment of appropriate reactive groups onto the chain. See, Chrisey et al. *Nucleic Acids Res.* 24:3031-3039 (1996). Methods for attaching antibodies to surfaces are also known in the art. See, Delamarche et al. *Langmuir* 12:1944-1946 (1996).

In another exemplary embodiment, the chip of this invention is an oligonucleotide array in which the binding functionality at each addressable location in the array comprises a nucleic acid having a particular nucleotide sequence. In particular, the array can comprise oligonucleotides. For example, the oligonucleotides could be selected so as to cover the sequence of a particular gene of interest. Alternatively, the array can comprise cDNA or EST sequences useful for expression profiling.

In another exemplary embodiment, the binding functionality is a drug moiety or a pharmacophore derived from a drug moiety. The drug moieties can be agents already accepted for clinical use or they can be drugs whose use is experimental, or whose activity or mechanism of action is under investigation. The drug moieties can have a proven action in a given disease state or can be only hypothesized to show desirable action in a given disease state. In a preferred embodiment, the drug moieties are compounds, which are being screened for their ability to interact with a target of choice. As such, drug moieties, which are useful in practicing the instant invention include drugs from a broad range of drug classes having a variety of pharmacological activities.

Exemplary classes of useful agents include, but are not limited to, non-steroidal anti-inflammatory drugs (NSAIDS). The NSAIDS can, for example, be selected from the following categories: (e.g., propionic acid derivatives, acetic acid derivatives, fenamic acid derivatives, biphenylcarboxylic acid derivatives and oxicams); steroidal anti-inflammatory drugs including hydrocortisone and the like; antihistaminic drugs (e.g., chlorpheniramine, triprolidine); antitussive drugs (e.g., dextromethorphan, codeine, carmiphen and carbetapentane); antipruritic drugs (e.g., methidilizine and trimeprizine); anticholinergic drugs (e.g., scopolamine, atropine, homatropine, levodopa); anti-emetic and antinauseant drugs (e.g., cyclizine, meclizine, chlorpromazine, buclizine); anorexic drugs (e.g., benzphetamine, phentermine, chlorphentermine, fenfluramine); central stimulant drugs (e.g., amphetamine, methamphetamine, dextroamphetamine and methylphenidate); antiarrhythmic drugs (e.g., propanolol, procainamide, disopyraminde, quinidine, encainide); β-adrenergic blocker drugs (e.g., metoprolol, acebutolol, betaxolol, labetalol and timolol); cardiotonic drugs (e.g., milrinone, amrinone and dobutamine); antihypertensive drugs (e.g., enalapril, clonidine, hydralazine, minoxidil, guanadrel, guanethidine);diuretic drugs (e.g., amiloride and hydrochlorothiazide); vasodilator drugs (e.g., diltazem, amiodarone, isosuprine, nylidrin, tolazoline and verapamil); vasoconstrictor drugs (e.g., dihydroergotamine, ergotamine and methylsergide); antiulcer drugs (e.g., ranitidine and cimetidine); anesthetic drugs (e.g., lidocaine, bupivacaine, chlorprocaine, dibucaine); antidepressant drugs (e.g., imipramine, desipramine, amitryptiline, nortryptiline); tranquilizer and sedative drugs (e.g., chlordiazepoxide, benacytyzine, benzquinamide, flurazapam, hydroxyzine, loxapine and promazine); antipsychotic drugs (e.g., chlorprothixene, fluphenazine, haloperidol, molindone, thioridazine and trifluoperazine); antimicrobial drugs (antibacterial, antifungal, antiprotozoal and antiviral drugs).

Antimicrobial drugs which are preferred for incorporation into the present composition include, for example, pharmaceutically acceptable salts of β-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, hexamidine isothionate, metronidazole, pentamidine, gentamycin, kanamycin, lineomycin, methacycline, methenamine, minocycline, neomycin, netilmycin, paromomycin, streptomycin, tobramycin, miconazole and amanfadine.

Other drug moieties of use in practicing the present invention include antineoplastic drugs (e.g., antiandrogens (e.g., leuprolide or flutamide), cytocidal agents (e.g., adriamycin, doxorubicin, taxol, cyclophosphamide, busulfan, cisplatin, α-2-interferon) anti-estrogens (e.g., tamoxifen), antimetabolites (e.g., fluorouracil, methotrexate, mercaptopurine, thioguanine).

The binding functionality can also comprise hormones (e.g., medroxyprogesterone estradiol, leuprolide, megestrol, octreotide or somatostatin); muscle relaxant drugs (e.g., cinnamedrine, cyclobenzaprine, flavoxate, orphenadrine, papaverine, mebeverine, idaverine, ritodrine, dephenoxylate, dantrolene and azumolen); antispasmodic drugs; bone-active drugs (e.g., diphosphonate and phosphonoalkylphosphinate drug compounds); endocrine modulating drugs (e.g., contraceptives (e.g., ethinodiol, ethinyl estradiol, norethindrone, mestranol, desogestrel, medroxyprogesterone), modulators of diabetes (e.g., glyburide or chlorpropamide), anabolics, such as testolactone or stanozolol, androgens (e.g., methyltestosterone, testosterone or fluoxymesterone), antiidiuretics (e.g., desmopressin) and calcitonins).

Also of use in the present invention are estrogens (e.g., diethylstilbesterol), glucocorticoids (e.g., triamcinolone, betamethasone, etc.) and progenstogens, such as norethindrone, ethynodiol, norethindrone, levonorgestrel; thyroid agents (e.g., liothyronine or levothyroxine) or anti-thyroid agents (e.g., methimazole); antihyperprolactinemic drugs (e.g., cabergoline); hormone suppressors (e.g., danazol or goserelin), oxytocics (e.g., methylergonovine or oxytocin) and prostaglandins, such as mioprostol, alprostadil or dinoprostone, can also be employed.

Other useful binding functionalities include immunomodulating drugs (e.g., antihistamines, mast cell stabilizers, such as lodoxamide and/or cromolyn, steroids (e.g., triamcinolone, beclomethazone, cortisone, dexamethasone, prednisolone, methylprednisolone, beclomethasone, or clobetasol), histamine $H_2$ antagonists (e.g., famotidine, cimetidine, ranitidine), immunosuppressants (e.g., azathioprine, cyclosporin), etc. Groups with anti-inflammatory activity, such as sulindac, etodolac, ketoprofen and ketorolac, are also of use. Other drugs of use in conjunction with the present invention will be apparent to those of skill in the art.

When the binding functionality is a chelating agent, crown ether or cyclodextrin, host-guest chemistry will dominate the interaction between the binding functionality and the target. The use of host-guest chemistry allows a great degree of affinity-moiety-target specificity to be engineered into a device of the invention. The use of these compounds to bind to specific compounds is well known to those of skill in the art. See, for example, Pitt et al. "The Design of Chelating Agents for the Treatment of Iron Overload," In, Inorganic Chemistry in Biology and Medicine; Martell, A. E., Ed.; American Chemical Society, Washington, D.C., 1980, pp. 279-312; Lindoy, L. F., THE Chemistry of Macrocyclic Ligand Complexes; Cambridge University Press, Cambridge, 1989; Dugas, H., Bioorganic Chemistry; Springer-Verlag, New York, 1989, and references contained therein.

Additionally, a number of routes allowing the attachment of chelating agents, crown ethers and cyclodextrins to other molecules is available to those of skill in the art. See, for example, Meares et al., "Properties of In vivo Chelate-Tagged Proteins and Polypeptides."In, Modification of Proteins: Food, Nutritional, and Pharmacological Aspects;" Feeney, R. E., Whitaker, J. R., Eds., American Chemical Society, Washington, D.C., 1982, pp. 370-387; Kasina et al. *Bioconjugate Chem.* 9:108-117 (1998); Song et al., *Bioconjugate Chem.* 8:249-255 (1997).

In an exemplary embodiment, the binding functionality is a polyaminocarboxylate chelating agent such as ethylenediaminetetraacetic acid (EDTA) or diethylenetriaminepentaacetic acid (DTPA), which is attached to an amine on the substrate, or spacer arm, by utilizing the commercially available dianhydride (Aldrich Chemical Co., Milwaukee, Wis.). When complexed with a metal ion, the metal chelate binds to tagged species, such as polyhistidyl-tagged proteins, which can be used to recognize and bind target species. Alternatively, the metal ion itself, or a species complexing the metal ion can be the target.

In a further exemplary embodiment, the binding functionality forms an inclusion complex with the target of interest. In a preferred embodiment, the binding functionality is a cyclodextrin or modified cyclodextrin. Cyclodextrins are a group of cyclic oligosaccharides produced by numerous microorganisms. Cyclodextrins have a ring structure which has a basket-like shape. This shape allows cyclodextrins to include many kinds of molecules into their internal cavity. See, for example, Szejtli, J., Cyclodextrins and Their Inclusion Complexes; Akademiai Klado, Budapest, 1982; and Bender et al., Cyclodextrin Chemistry, Springer-Verlag, Berlin, 1978. Cyclodextrins are able to form inclusion complexes with an array of organic molecules including, for example, drugs, pesticides, herbicides and agents of war. See, Tenjarla et al., *J. Pharm. Sci.* 87:425-429 (1998); Zughul et al., *Pharm. Dev. Technol.* 3:43-53 (1998); and Albers et al., *Crit. Rev. Ther. Drug Carrier Syst.* 12:311-337 (1995). Importantly, cyclodextrins are able to discriminate between enantiomers of compounds in their inclusion complexes. Thus, in one preferred embodiment, the invention provides for the detection of a particular enantiomer in a mixture of enantiomers. See, Koppenhoefer et al. *J. Chromatogr. A* 793:153-164 (1998). The cyclodextrin binding functionality can be attached to a spacer arm or directly to the substrate. See, Yamamoto et al., *J. Phys. Chem. B* 101:6855-6860 (1997). Methods to attach cyclodextrins to other molecules are well known to those of skill in the chromatographic and pharmaceutical arts. See, Sreenivasan, K. J. *Appl. Polym. Sci.* 60:2245-2249 (1996).

In a further preferred embodiment, the binding functionality is selected from nucleic acid species, such as aptamers and aptazymes that recognize specific targets.

Targets

The methods of the present invention can be used to detect any target, or class of targets, which interact with a binding functionality in a detectable manner. The interaction between the target and binding functionality can be any physicochemical interaction, including covalent bonding, ionic bonding, hydrogen bonding, van der Waals interactions, attractive electronic interactions and hydrophobic/hydrophilic interactions.

In an exemplary embodiment, the interaction is an ionic interaction. In this embodiment, an acid, base, metal ion or metal ion-binding ligand is the target. In a further exemplary embodiment, the interaction is a hydrogen bonding interaction.

In a preferred embodiment, the target molecule is a biomolecule such as a polypeptide (e.g., peptide or protein), a polynucleotide (e.g., oligonucleotide or nucleic acid), a carbohydrate (e.g., simple or complex carbohydrate) or a lipid (e.g., fatty acid or polyglycerides, phospholipids, etc.). In the case of proteins, the nature of the target can depend upon the nature of the binding functionality. For example, one can capture a ligand using a receptor for the ligand as a binding functionality; an antigen using an antibody against the antigen, or a substrate using an enzyme that acts on the substrate.

The target can be derived from any sort of biological source, including body fluids such as blood, serum, saliva, urine, seminal fluid, seminal plasma, lymph, and the like. It also includes extracts from biological samples, such as cell lysates, cell culture media, or the like. For example, cell lysate samples are optionally derived from, e.g., primary tissue or cells, cultured tissue or cells, normal tissue or cells, diseased tissue or cells, benign tissue or cells, cancerous tissue or cells, salivary glandular tissue or cells, intestinal tissue or cells, neural tissue or cells, renal tissue or cells, lymphatic tissue or cells, bladder tissue or cells, prostatic tissue or cells, urogenital tissues or cells, tumoral tissue or cells, tumoral neovasculature tissue or cells, or the like.

In another embodiment, the target is a member selected from the group consisting of acids, bases, organic ions, inorganic ions, pharmaceuticals, herbicides, pesticides, and noxious gases. Each of these targets can be detected as a vapor or a liquid. The target can be present as a component in a mixture of structurally unrelated compounds, an assay mixture, racemic mixtures of stereoisomers, non-racemic mixtures of stereoisomers, mixtures of diastereomers, mixtures of positional isomers or as a pure compound. Within the scope of the invention is method to detect a particular target of interest without interference from other substances within a mixture.

The target can be labeled with a fluorophore or other detectable group either directly or indirectly through interacting with a second species to which a detectable group is bound. When a second labeled species is used as an indirect labeling agent, it is selected from any species that is known to interact with the target species. Preferred second labeled species include, but are not limited to, antibodies, aptazymes, aptamers, streptavidin, and biotin.

The target can be labeled either before or after it interacts with the binding functionality. The target molecule can be labeled with a detectable group or more than one detectable group. Where the target species is multiply labeled with more than one detectable group, the groups are preferably distinguishable from each other.

Organic ions, which are substantially non-acidic and non-basic (e.g., quaternary alkylammonium salts) can be detected by a binding functionality. For example, a binding functionality with ion exchange properties is useful in the present invention. A specific example is the exchange of a cation such as dodecyltrimethylammonium cation for a metal ion such as sodium, using a spacer arm presenting a negatively charged species. Binding functionalities that form inclusion complexes with organic cations are also of use. For example, crown ethers and cryptands can be used to form inclusion complexes with organic ions such as quaternary ammonium cations.

Inorganic ions such as metal ions and complex ions (e.g., $SO_4^{-2}$, $PO_4^{-3}$) can also be detected using the device and method of the invention. Metal ions can be detected, for example, by their complexation or chelation by agents bound to the adsorbent layer. In this embodiment, the binding functionality can be a simple complexing moiety (e.g., carboxylate, amine, thiol) or can be a more structurally complicated agent (e.g., ethylenediaminepentaacetic acid, crown ethers, aza crowns, thia crowns).

Complex inorganic ions can be detected by, for example, their ability to compete with ligands for bound metal ions in ligand-metal complexes. When a ligand bound to a spacer arm or a substrate forms a metal-complex having a thermodynamic stability constant, which is less than that of the complex between the metal and the complex ion, the complex ion will replace the metal ion on the immobilized ligand. Methods of determining stability constants for compounds formed between metal ions and ligands are well known to those of skill in the art. Using these stability constants, substrates including affinity moieties that are specific for particular ions can be manufactured. See, Martell, A. E., Motekaitis, R. J., Determination and Use of Stability Constants, 2d Ed., VCH Publishers, New York 1992.

Small molecules such as pesticides, herbicides, and the like can be detected by the use of a number of different binding functionality motifs. Acidic or basic components can be detected as described above. A target's metal binding capability can also be used to advantage, as described above for complex ions. Additionally, if these targets bind to an identified biological structure (e.g., a receptor), the receptor can be immobilized on the substrate, a spacer arm. Techniques are also available in the art for raising antibodies which are highly specific for a particular species. Thus, it is within the scope of the present invention to make use of antibodies against small molecules, pesticides, agents of war and the like for detection of those species. Techniques for raising antibodies to herbicides and pesticides are known to those of skill in the art. See, Harlow, Lane, Monoclonal Antibodies: A Laboratory Manual, Cold Springs Harbor Laboratory, Long Island, N.Y., 1988.

In another exemplary embodiment, the target is detected by binding to an immobilized binding functionality is an organophosphorous compound such as an insecticide.

Methods of Making

Figure 4:
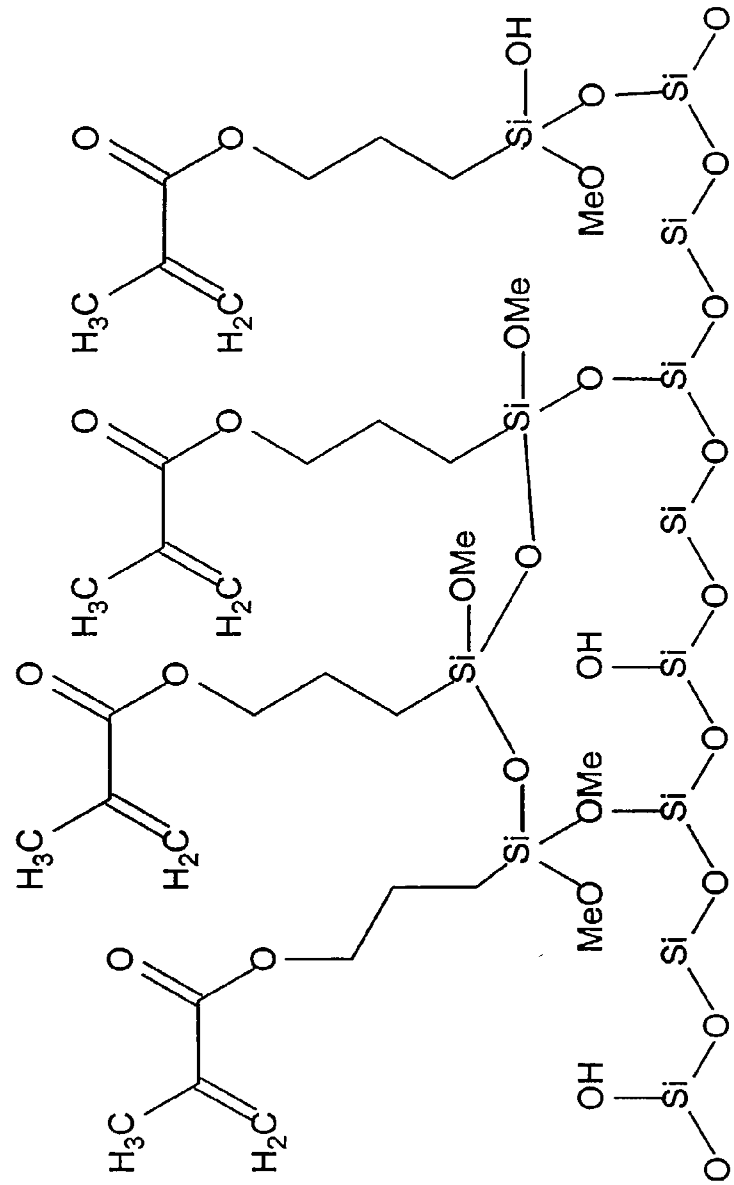
FIG. 4 is a schematic drawing of a chip surface having the agent of FIG. 3 bound thereto.
Figure 5:
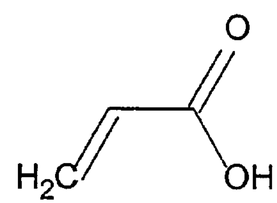
FIG. 5 sets forth the structures of two exemplary monomers of use in forming the linker arms.
Figure 5:
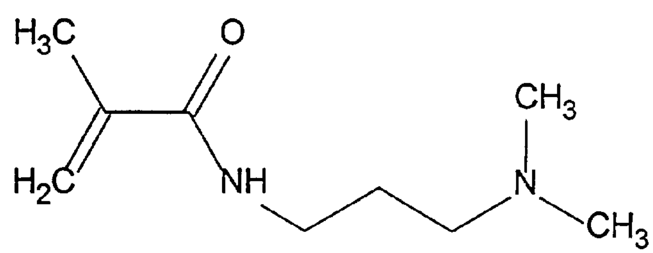
Figure 6:
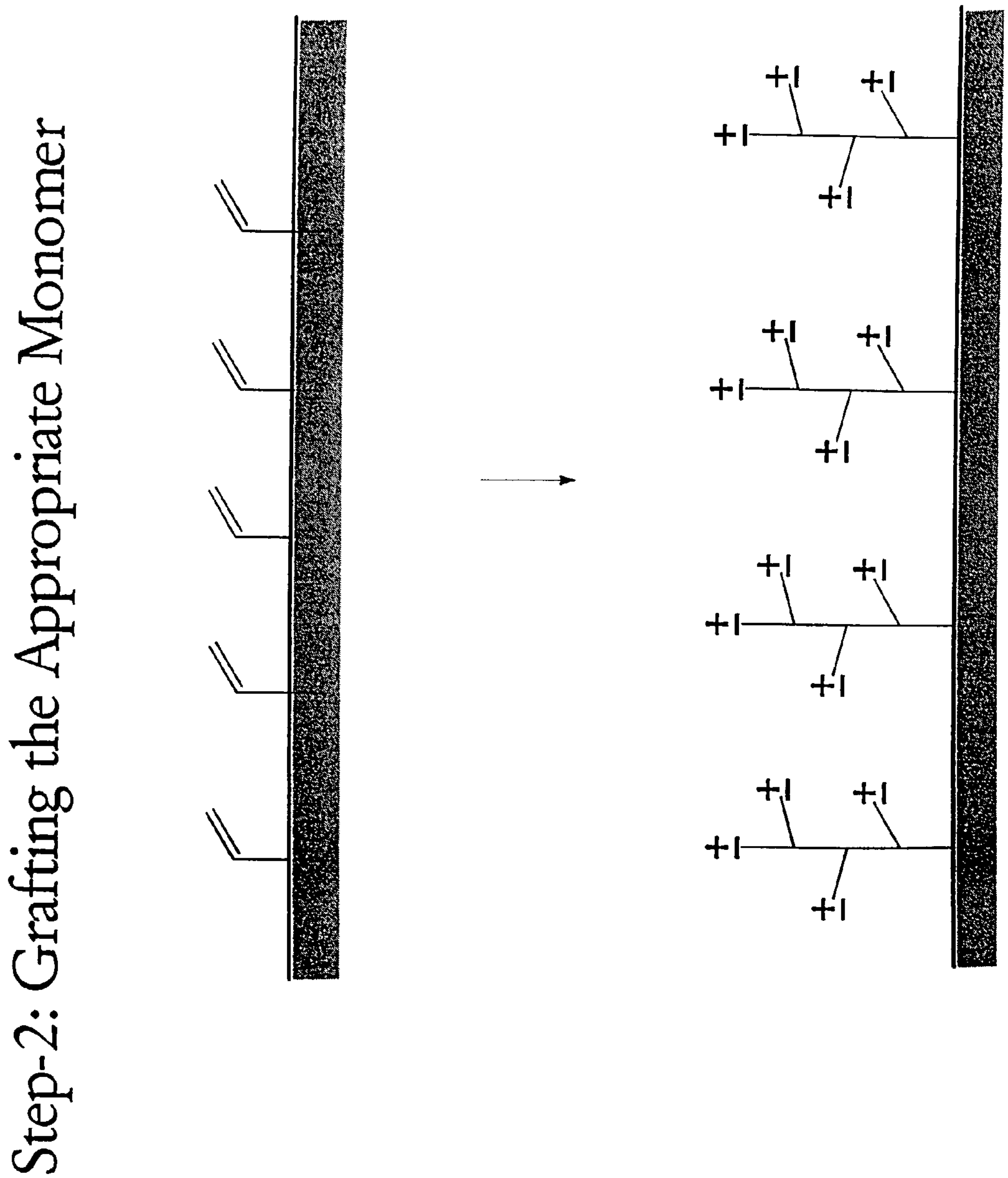
FIG. 6 is a schematic diagram showing the grafting of the linker arms onto the anchor moiety, providing a surface having a charged polymer bound thereto.
Figure 7:
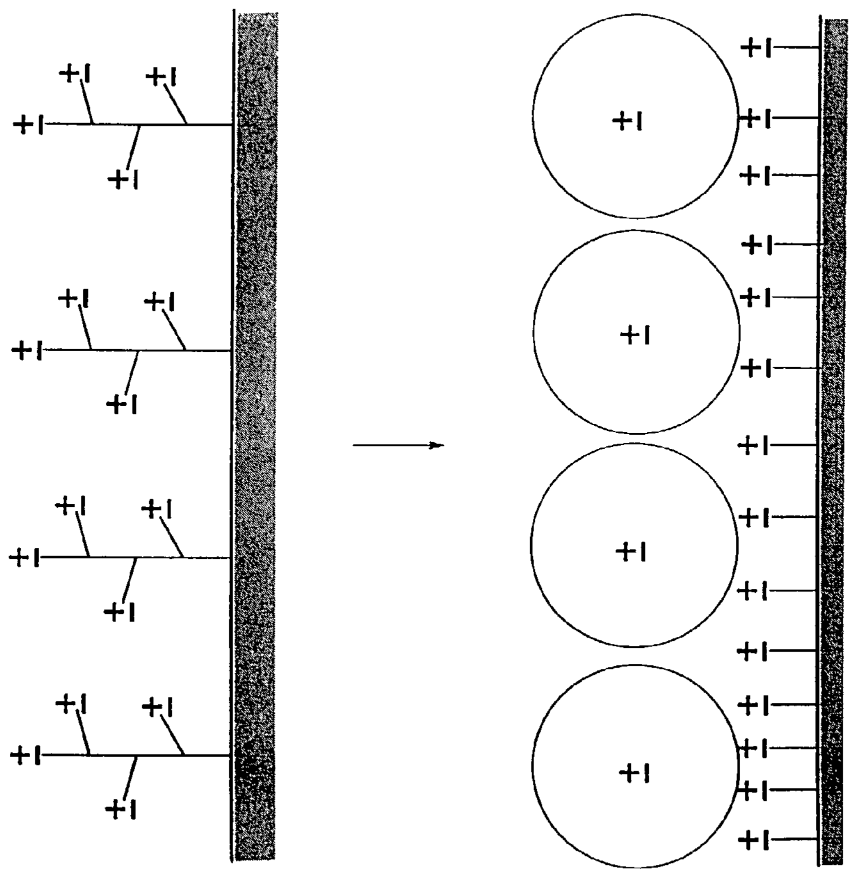
FIG. 7 is a schematic diagram showing the attachment of the components of the adsorbent film onto the film support of linker arms via electrostatic attraction between the film components and the film support.

An exemplary method for preparing a chip of the invention is illustrated by reference to FIG. 3 to FIG. 7. In this representative example, the chip of the invention utilizes an aluminum substrate coated with silicon dioxide according to art-recognized methods. The substate is then derivatized with an organosilane such as (3-methacryloxypropyl)-trimethoxysilane (FIG. 3) to secure the anchor moiety to the substrate surface (FIG. 4). Following the immobilization of the anchor moiety, the chip surface is contacted with a suitable monomer (e.g. acrylic acid or derivatives thereof (FIG. 5)), which serves as the origin point for the assembly of the film support by polymerization grafting (FIG. 6). Following the grafting process, the particles of the adsorbent film are immobilized onto the linker arm through electrostatic attraction between the particle and the linker arm (FIG. 7).

Figure 8:
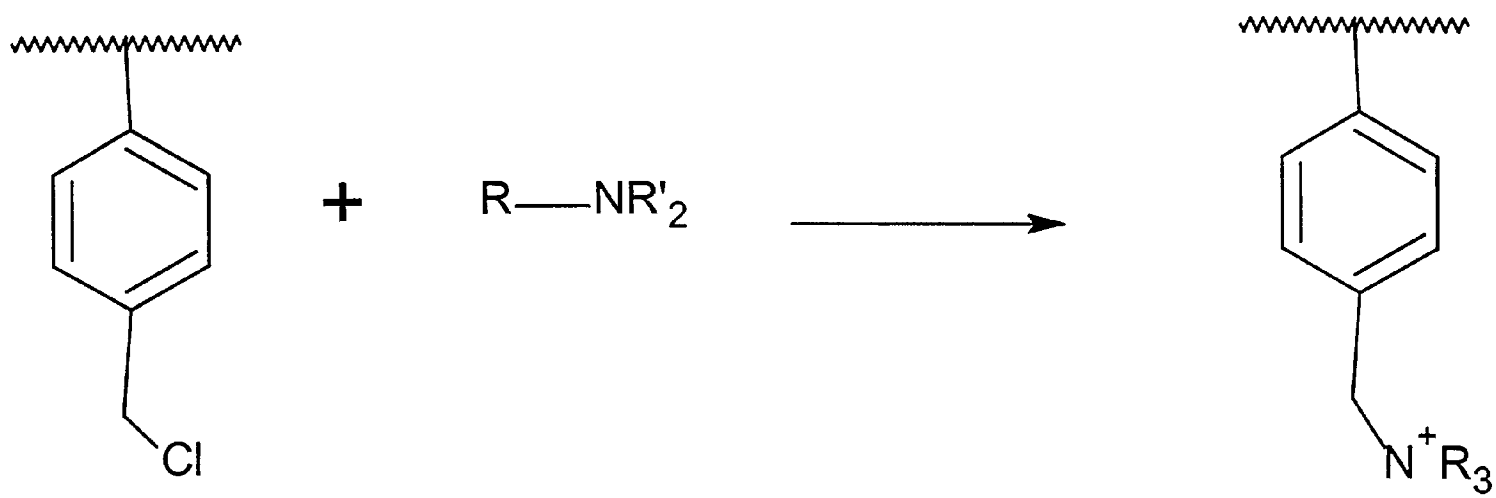
FIG. 8 is a reaction scheme showing the reaction between a reactive functional group on a component of the adsorbent film and a tertiary amine to form a quaternary amine binding functionality.

Exemplary particles of the adsorbent film useful in the present invention are those that are amenable to alteration of the binding functionality of the particles. In a representative embodiment, the particle includes a backbone moiety that includes a pendent benzyl chloride group, which is available for reactions elaborating the active benzylic carbon center. For example, a positively charged binding functionality is readily prepared by forming an adduct between a tertiary amine and the benzylic carbon center as shown in FIG. 8.

Figure 9:
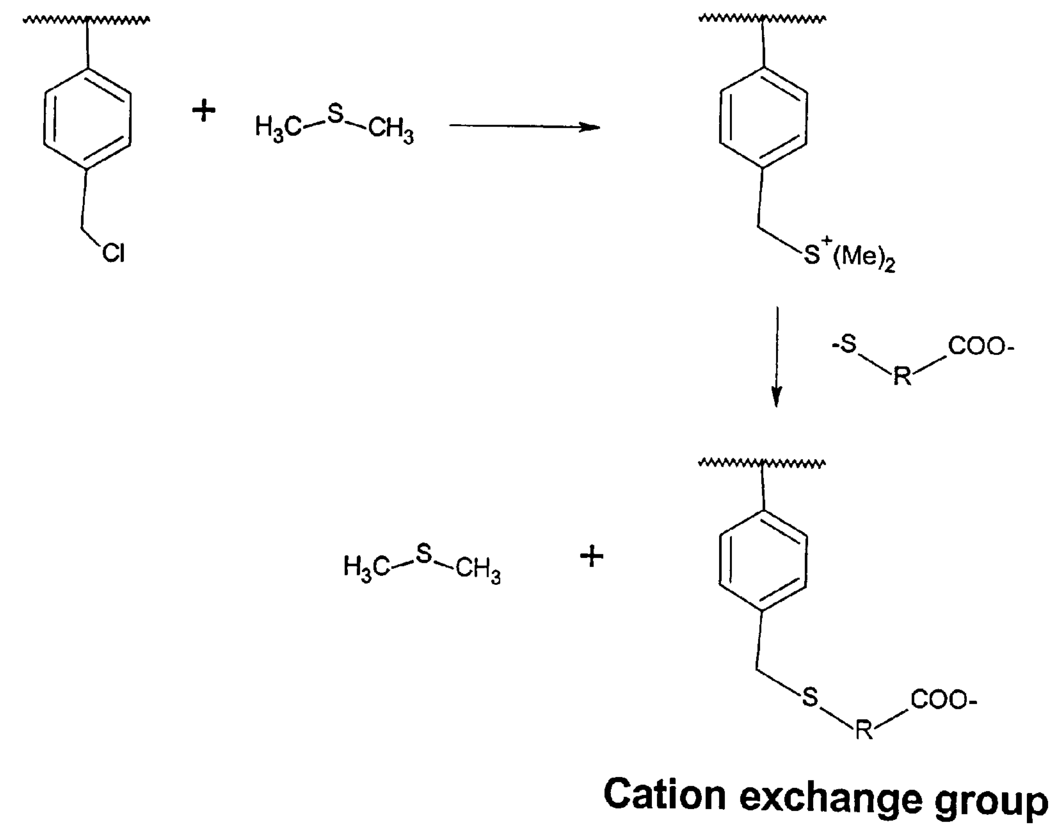
FIG. 9 is a reaction scheme showing the reaction between a reactive functional group on a component of the adsorbent film and a carboxylate-bearing species to form a carboxylate binding functionality.
Figure 10:
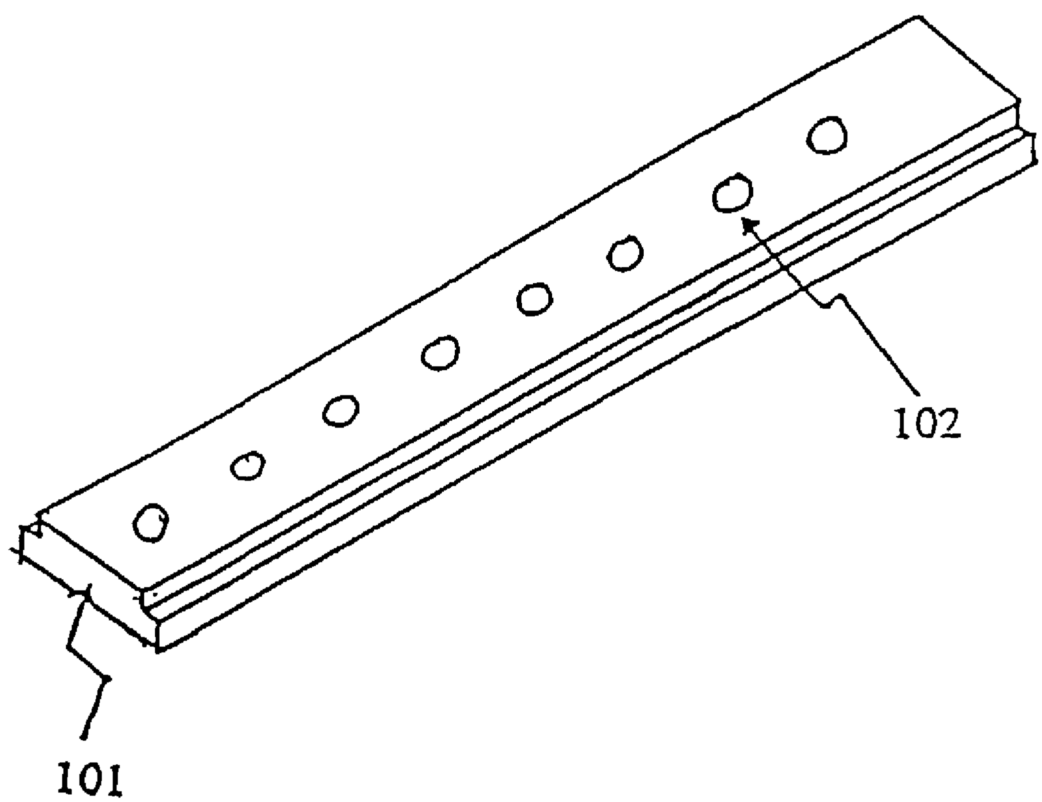
FIG. 10 depicts a chip comprising a substrate 101 and discontinuous spots of an adsorbent layer 102.

A representative positively charged binding functionality can be incorporated into a component of the adsorbent film by a method such as that set forth in FIG. 9. The benzyl chloride moiety is reacted with a sulfide. The intermediate adduct is reacted with a carboxylate-bearing species, forming a carboxylate derivatized component of the adsorbent film.

The grafting process is accomplished using a number of possible synthetic routes including, but not limited to, radical thermal polymerization using a thermal initiator, radical photopolymerization with a photoinitiator, radical thermal polymerization without a thermal initiator, atom transfer radical polymerization, anionic polymerization, cationic polymerization and condensation polymerization. Suitable monomers are dependent upon the type of polymerization being utilized, and it is within the abilities of one of skill in the art to select the proper monomer and polymerization conditions to achieve a desired property or result.

When radical thermal polymerization with a thermal initiator, or radical photopolymerization with a photoinitiator is utilized, a wide variety of functional monomers are available for this purpose. Suitable monomers include, but are not limited to, styrenic or acrylic monomers with anionic or cationic functional groups. In general, it is preferred to use monomers, which are weakly acidic or weakly basic although monomers which are strongly acidic or strongly basic may also be used.

When the adsorbent layer bears an overall positive charge, a representative film support is based on a carboxylate-based compound, such as acrylic acid. Conversely, when the adsorbent layer has an overall anionic charge, a representative film support is based on a quaternary ammonium-containing compound, such as N-[3-(dimethylamino)propyl]methacrylamide.

To prepare the film support, a solution of a suitable ionizable monomer is mixed with a suitable initiator and diluted with water. An aliquot of the resulting solution is then deposited on the chip surface at the location of the intended coupling side for the adsorbent film. If a photoinitiator is used, the chip is then placed in an airtight container with a UV transparent lid, the container is briefly sparged to displace any residual oxygen in the polymerization chamber, the container vent lines are then closed, and the container placed under a suitable UV light source in order to couple the monomer to the anchor moiety. After the photopolymerization step, the chip surface is then rinsed to remove any residual oligomeric fragments and then allowed to dry.

While components of the adsorbent film can be derived from a number of synthetic sources, the preferred route to synthesis of such material is the use of emulsion polymerization to produce a suspension of particles of suitable reactive polymer. Although a number of reactive monomers are potentially suitable for producing such a latex, commercially available reactive monomers, such as vinylbenzyl chloride and glycidyl methacrylate are preferred. Of these, vinylbenzyl chloride is particularly preferred because of its chemical stability with respect to chemical modification subsequent to the latex synthesis step. Another highly desirable monomer is vinylbenzyl glycidyl ether, which exhibits excellent chemical stability and is somewhat more hydrophilic than vinylbenzyl chloride. Other useful methods of preparing the components of the adsorbent film are known in the art (see, for example, U.S. Pat. Nos. 4,101,460; 4,383,047; 4,252,644; 4,351,909; 4,101,460 and 5,324,752).

In an exemplary embodiment, a functionalized monomer, bearing the binding functionality, either protected or not, are mixed with at least one other suitable monomer and polymerized into polymers containing the binding functionality. The polymers can then be deprotected, if necessary.

Certain particles useful in forming the adsorbent film are substantially solid, while others may be permeable or hollow. U.S. Pat. No. 4,880,842 discloses a process for making hollow latexes by introducing a non-polymeric acid to an early stage of the multi-stage polymer particles instead of copolymerizing acid to make swellable cores. This method for preparing hollow latexes requires cores containing acid or acidic monomers to enable swelling to occur at room temperature.

In latexes the particles are formed by chemical synthesis. In resins the particles are formed by suspension polymerization, e.g., by mechanical shearing.

After synthesis, the adsorbent film components can be further elaborated by a variety of chemical reactions well known to those skilled in the art. For example, in order to produce an anion exchange hydrogel particle, the latex slurry is mixed with a suitable amine (e.g. dimethylethanol amine or trimethyl amine) and allowed to react to produce a quaternary ion exchange site. Production of an analogous particle, containing cation exchange sites can be accomplished by a number of well-known synthetic schemes. A particularly versatile method relies on the use of a dimethyl sulfide displacement reaction, in which vinylbenzyl chloride latex is first reacted with a solution of dimethyl sulfide. The resulting reaction product is a sulfonium based anion exchange hydrogel particle. A second cation exchange site generation reagent is then added to the reaction mixture which can be heated in order to help drive the reaction to completion. An exemplary reagent for this purpose is mercaptopropionic acid. A solution of this acid is first pH adjusted to about 11 and then mixed with the above suspension of sulfonium based anion exchange hydrogel particles. After heating the suspension at about 70° C. for a predetermined period of time, the substitution reaction is complete and the resulting adsorbent film component is now a weak acid cation exchange particle.

Similar reaction pathways are available for preparing adsorbent film components with other binding functionalities. It is within the abilities of one of skill in the art to determine an appropriate reaction pathway to conjugate a selected binding functionality to the adsorbent film components of use in the chips of the invention (see, for example, Hermanson, BIOCONJUGATE TECHNIQUES, Academic Press, San Diego, 1996; and Dunn et al., Eds. POLYMERIC DRUGS AND DRUG DELIVERY SYSTEMS, ACS Symposium Series Vol. 469, American Chemical Society, Washington, D.C. 1991.

Following the synthesis and functionalization steps set forth above, the adsorbent film components are coated onto the chip derivatized with the linker arm. Thus, a slurry of coating particles is aliquoted onto the chip surface at the location of the previously grafted, oppositely charged linker arm. The slurry of particles is allowed to react for a few seconds and then the residual unattached particles are simply rinsed away.

Method for Synthesizing the Adsorbent Film Comprising Larger Adsorbent Particles The adsorbent film comprises adsorbent particles as described above. Large adsorbent particles, with diameters at least about 1 μm, are preferred. Exemplary particles include those with diameters of from about 1 μm to about 100 μm. Larger adsorbent particles enable adsorbent chips of the present invention to have a higher capacity.

In an exemplary embodiment, a plurality of functionalized monomers, bearing the binding functionality, either protected or not, are contacted with a seed component. The seed component absorbs the functionalized monomers to form a monomer-polymer solution. In a preferred embodiment, the monomer-polymer solution grows to from about 100 to 1000 times the original size of the seed component. After formation of the monomer-polymer solution, the solution is polymerized by appropriate means.

Preferred reactive monomers suitable for producing large adsorbent particles include vinylbenzyl chloride and glycidyl methacrylate. Of these, vinylbenzyl chloride is particularly preferred because of its chemical stability with respect to chemical modification subsequent to the latex synthesis step. Another highly desirable monomer is vinylbenzyl glycidyl ether, which exhibits excellent chemical stability and is somewhat more hydrophilic than vinylbenzyl chloride. Other useful methods of preparing the components of the adsorbent film are known in the art (see, for example, U.S. Pat. Nos. 4,101,460; 4,383,047; 4,252,644; 4,351,909; 4,101,460 and 5,324,752).

After synthesis, the adsorbent film components can be further elaborated, i.e., functionalized, by a variety of chemical reactions well known to those skilled in the art and described above and in the Examples. As discussed in the preceding sections, the process of elaboration generally results in a particle that is about 1 to about 2 orders of magnitude larger in diameter than the unfunctionalized starting particle.

Following the synthesis and functionalization steps set forth above, the adsorbent film components are coated onto the chip derivatized with the linker arm. Thus, a slurry of coating particles is aliquoted onto the chip surface at the location of the previously grafted, oppositely charged linker arm. The slurry of particles is allowed to react for a few seconds and then the residual unattached particles are simply rinsed away.

Methods of Using the Chips

Binding-pair (also known as ligand-receptor, molecular recognition binding and the like) techniques play an important role in many applications of biomedical analysis and are gaining importance in the fields of environmental science, veterinary medicine, pharmaceutical research, food and water quality control, etc.

The chip of the present invention is useful in performing assays of substantially any format including, but not limited to chromatographic capture, immunoassays, competitive assays, DNA or RNA binding assays, fluorescence in situ hybridization (FISH), protein and nucleic acid profiling assays, sandwich assays and the like. The following discussion focuses on the use of the methods of the invention in practicing exemplary assays. This focus is for clarity of illustration only and is not intended to define or limit the scope of the invention. Those of skill in the art will appreciate that the method of the invention is broadly applicable to any assay technique for detecting the presence and/or amount of a target.

The chip of the present invention is useful for performing retentate chromatography. Retentate chromatography has many uses in biology and medicine. These uses include combinatorial biochemical separation and purification of analytes, protein profiling of biological samples, the study of differential protein expression and molecular recognition events, diagnostics and drug discovery.

One basic use of retentate chromatography as an analytical tool involves exposing a sample to a combinatorial assortment of different adsorbent/eluant combinations and detecting the behavior of the analyte under the different conditions. This both purifies the analyte and identifies conditions useful for detecting the analyte in a sample. Substrates having adsorbents identified in this way can be used as specific detectors of the analyte or analytes. In a progressive extraction method, a sample is exposed to a first adsorbent/eluant combination and the wash, depleted of analytes that are adsorbed by the first adsorbent, is exposed to a second adsorbent to deplete it of other analytes. Selectivity conditions identified to retain analytes also can be used in preparative purification procedures in which an impure sample containing an analyte is exposed, sequentially, to adsorbents that retain it, impurities are removed, and the retained analyte is collected from the adsorbent for a subsequent round. See, for example, U.S. Pat. No. 6,225,047.

The chip of the invention is useful in applications such as sequential extraction of analytes from a solution, progressive resolution of analytes in a sample, preparative purification of an analyte, making probes for specific detection of analytes, methods for identifying proteins, methods for assembling multimeric molecules, methods for performing enzyme assays, methods for identifying analytes that are differentially expressed between biological sources, methods for identifying ligands for a receptor, methods for drug discovery (e.g., screening assays), and methods for generating agents that specifically bind an analyte.

In other applications, chip-based assays based on specific binding reactions are useful to detect a wide variety of targets such as drugs, hormones, enzymes, proteins, antibodies, and infectious agents in various biological fluids and tissue samples. In general, the assays consist of a target, a binding functionality for the target, and a means of detecting the target after its immobilization by the binding functionality (e.g., a detectable label). Immunological assays involve reactions between immunoglobulins (antibodies), which are capable of binding with specific antigenic determinants of various compounds and materials (antigens). Other types of reactions include binding between avidin and biotin, protein A and immunoglobulins, lectins and sugar moieties and the like. See, for example, U.S. Pat. No. 4,313,734, issued to Leuvering; U.S. Pat. No. 4,435,504, issued to Zuk; U.S. Pat. Nos. 4,452,901 and 4,960,691, issued to Gordon; and U.S. Pat. No. 3,893,808, issued to Campbell.

The present invention provides a chip useful for performing assays that are useful for confirming the presence or absence of a target in a sample and for quantitating a target in a sample. An exemplary assay format with which the invention can be used is an immunoassay, e.g., competitive assays, and sandwich assays. The invention is further illustrated using these two assay formats. The focus of the following discussion on competitive assays and sandwich assays is for clarity of illustration and is not intended to either define or limit the scope of the invention. Those of skill in the art will appreciate that the invention described herein can be practiced in conjunction with a number of other assay formats.

In an exemplary competitive binding assay, two species, one of which is the target, compete for a binding functionality on an adsorbent film. After an incubation period, unbound materials are washed off and the amount of target, or other species bound to the functionality is compared to reference amounts for determination of the target, or other species concentration in the assay mixture. Other competitive assay motifs using labeled target and/or labeled binding functionality and/or labeled reagents will be apparent to those of skill in the art.

A second type of assay is known as a sandwich assay and generally involves contacting an assay mixture with a surface having immobilized thereon a first binding functionality immunologically specific for that target. A second solution comprising a detectable binding material is then added to the assay. The labeled binding material will bind to a target, which is bound to the binding functionality. The assay system is then subjected to a wash step to remove labeled binding material, which failed to bind with the target and the amount of detectable material remaining on the chip is ordinarily proportional to the amount of bound target. In representative assays one or more of the target, binding functionality or binding material is labeled with a fluorescent label.

In addition to detecting an interaction between a binding functionality and a target, it is frequently desired to quantitate the magnitude of the affinity between two or more binding partners. The format of an assay for extracting affinity data for two molecules can be understood by reference to an embodiment in which a ligand that is known to bind to a receptor is displaced by an antagonist to that receptor. Other variations on this format will be apparent to those of skill in the art. The competitive format is well known to those of skill in the art. See, for example, U.S. Pat. Nos. 3,654,090 and 3,850,752.

The binding of an antagonist to a receptor can be assayed by a competitive binding method using a ligand for that receptor and the antagonist. One of the three binding partners (i.e., the ligand, antagonist or receptor) is bound to the binding functionality, or is the binding functionality. In an exemplary embodiment, the receptor is bound to the adsorbent film. Various concentrations of ligand are added to different chip regions. A detectable antagonist is then applied to each region to a chosen final concentration. The treated chip will generally be incubated at room temperature for a preselected time. The receptor-bound antagonist can be separated from the unbound antagonist by filtration, washing or a combination of these techniques. Bound antagonist remaining on the chip can be measured as discussed herein. A number of variations on this general experimental procedure will be apparent to those of skill in the art.

Competition binding data can be analyzed by a number of techniques, including nonlinear least-squares curve fitting procedure. When the ligand is an antagonist for the receptor, this method provides the IC50 of the antagonist (concentration of the antagonist which inhibits specific binding of the ligand by 50% at equilibrium). The IC50 is related to the equilibrium dissociation constant (Ki) of the antagonist based on the Cheng and Prusoff equation: Ki=IC50/(1+L/Kd), where L is the concentration of the ligand used in the competitive binding assay, and Kd is the dissociation constant of the ligand as determined by Scatchard analysis. These assays are described, among other places, in Maddox et al., *J Exp Med.,* 158: 1211 (1983); Hampton et al., SEROLOGICAL METHODS, A LABORATORY MANUAL, APS Press, St. Paul, Minn., 1990.

The chip and method of the present invention are also of use in screening libraries of compounds, such as combinatorial libraries. The synthesis and screening of chemical libraries to identify compounds, which have novel bioactivities, and material science properties is now a common practice. Libraries that have been synthesized include, for example, collections of oligonucleotides, oligopeptides, and small and large molecular weight organic or inorganic molecules. See, Moran et al., PCT Publication WO 97/35198, published Sep. 25, 1997; Baindur et al., PCT Publication WO 96/40732, published Dec. 19, 1996; Gallop et al., *J. Med. Chem.* 37:1233-51 (1994).

Virtually any type of compound library can be probed using the method of the invention, including peptides, nucleic acids, saccharides, small and large molecular weight organic and inorganic compounds. In a presently preferred embodiment, the libraries synthesized comprise more than 10 unique compounds, preferably more than 100 unique compounds and more preferably more than 1000 unique compounds.

The nature of these libraries is better understood by reference to peptide-based combinatorial libraries as an example. The present invention is useful for assembling peptide-based combinatorial libraries, but it is not limited to these libraries. The methods of the invention can be used to screen libraries of essentially any molecular format, including small organic molecules, carbohydrates, nucleic acids, polymers, organometallic compounds and the like. Thus, the following discussion, while focusing on peptide libraries, is intended to be illustrative and not limiting.

Libraries of peptides and certain types of peptide mimetics, called "peptoids", are assembled and screened for a desirable biological activity by a range of methodologies (see, Gordon et al., *J. Med Chem.,* 37: 1385-1401 (1994); Geysen, (*Bioorg. Med. Chem. Letters,* 3: 397-404 (1993); *Proc. Natl. Acad Sci. USA,* 81: 3998 (1984); Houghton, *Proc. Natl. Acad. Sci. USA,* 82: 5131 (1985); Eichler et al., *Biochemistry,* 32: 11035-11041 (1993); and U.S. Pat. No. 4,631,211); Fodor et al., *Science,* 251: 767 (1991); Huebner et al. (U.S. Pat. No. 5,182,366). Small organic molecules have also been prepared by combinatorial means. See, for example, Camps. et al., *Annaks de Quimica,* 70: 848 (1990); U.S. Pat. No. 5,288,514; U.S. Pat. No. 5,324,483; Chen et al., *J. Am. Chem. Soc.,* 116: 2661-2662 (1994).

In an exemplary embodiment, a binding domain of a receptor, for example, serves as the focal point for a drug discovery assay, where, for example, the receptor is immobilized, and incubated both with agents (i.e., ligands) known to interact with the binding domain thereof, and a quantity of a particular drug or inhibitory agent under test. The extent to which the drug binds with the receptor and thereby inhibits receptor-ligand complex formation can then be measured. Such possibilities for drug discovery assays are contemplated herein and are considered within the scope of the present invention. Other focal points and appropriate assay formats will be apparent to those of skill in the art.

Detection

The presence of the analyte immobilized on the adsorbent film and changes in the adsorbent film upon binding of the analyte can be detected by the use of microscopes, spectrometry, electrical techniques and the like. For example, in certain embodiments light in the visible region of the spectrum is used to illuminate details of the adsorbent film (e.g., reflectance, transmittance, birefringence, diffraction, etc.). Alternatively, the light can be passed through the adsorbent film and the amount of light transmitted, absorbed or reflected can be measured. The device can utilize a backlighting device such as that described in U.S. Pat. No. 5,739,879. Light in the ultraviolet and infrared regions is also of use in the present invention.

For the detection of low concentrations of analytes in the field of diagnostics, the methods of chemiluminescence and electrochemiluminescence are gaining wide-spread use. These methods of chemiluminescence and electro-chemiluminescence provide a means to detect low concentrations of analytes by amplifying the number of luminescent molecules or photon generating events many-fold, the resulting "signal amplification" then allowing for detection of low concentration analytes.

In another embodiment, a fluorescent label is used to label one or more assay component or region of the chip. Fluorescent labels have the advantage of requiring few precautions in handling, and being amenable to high-throughput visualization techniques (optical analysis including digitization of the image for analysis in an integrated system comprising a computer). Preferred labels are typically characterized by one or more of the following: high sensitivity, high stability, low background, low environmental sensitivity and high specificity in labeling. Many fluorescent labels are commercially available from the SIGMA chemical company (Saint Louis, Mo.), Molecular Probes (Eugene, Oreg.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), and Applied Biosystems (Foster City, Calif.), as well as many other commercial sources known to one of skill. Furthermore, those of skill in the art will recognize how to select an appropriate fluorophore for a particular application and, if it not readily available commercially, will be able to synthesize the necessary fluorophore de novo or synthetically modify commercially available fluorescent compounds to arrive at the desired fluorescent label.

In addition to small molecule fluorophores, naturally occurring fluorescent proteins and engineered analogues of such proteins are useful in the present invention. Such proteins include, for example, green fluorescent proteins of cnidarians (Ward et al., *Photochem. Photobiol.* 35:803-808 (1982); Levine et al., *Comp. Biochem. Physiol.,* 72B:77-85 (1982)), yellow fluorescent protein from Vibrio fischeri strain (Baldwin et al., *Biochemistry* 29:5509-15 (1990)), Peridinin-chlorophyll from the dinoflagellate Symbiodinium sp. (Morris et al., *Plant Molecular Biology* 24:673:77 (1994)), phycobiliproteins from marine cyanobacteria, such as Synechococcus, e.g., phycoerythrin and phycocyanin (Wilbanks et al., *J. Biol. Chem.* 268:1226-35 (1993)), and the like.

Microscopic techniques of use in practicing the invention include, but are not limited to, simple light microscopy, confocal microscopy, polarized light microscopy, atomic force microscopy (Hu et al., *Langmuir* 13:5114-5119 (1997)), scanning tunneling microscopy (Evoy et al., *J. Vac. Sci. Technol A* 15:1438-1441, Part 2 (1997)), and the like.

Spectroscopic techniques of use in practicing the present invention include, for example, infrared spectroscopy (Zhao et al., *Langmuir* 13:2359-2362 (1997)), raman spectroscopy (Zhu et al., *Chem. Phys. Lett.* 265:334-340 (1997)), X-ray photoelectron spectroscopy (Jiang et al., *Bioelectroch. Bioener.* 42:15-23 (1997)) and the like. Visible and ultraviolet spectroscopies are also of use in the present invention.

Other useful techniques include, for example, surface plasmon resonance (Evans et al., *J. Phys. Chem. B* 101:2143-2148 (1997), ellipsometry (Harke et al., *Thin Solid Films* 285:412-416 (1996)), impedometric methods (Rickert et al., *Biosens. Bioelectron.* 11:757:768 (1996)), and the like.

In addition, the Polymerase Chain Reaction (PCR) and other related techniques have gained wide use for amplifying the number of nucleic acid analytes in a sample. By the addition of appropriate enzymes, reagents, and temperature cycling methods, the number of nucleic acid analyte molecules are amplified such that the analyte can be detected by most known detection means.

Of particular interest is the use of mass spectrometric techniques to detect analytes immobilized on the adsorbent film, particularly those mass spectrometric methods utilizing desorption of the analyte from the adsorbent and direct detection of the desorbed analytes. Analytes retained by the adsorbent after washing are adsorbed to the substrate. Analytes retained on the substrate are detected by desorption spectrometry.

Desorbing the analyte from the adsorbent involves exposing the analyte to an appropriate energy source. Usually this means striking the analyte with radiant energy or energetic particles. For example, the energy can be light energy in the form of laser energy (e.g., UV laser) or energy from a flash lamp. Alternatively, the energy can be a stream of fast atoms. Heat may also be used to induce/aid desorption.

The biochips of this invention are useful for surface-enhanced laser desorption/ionization, or SELDI. SELDI represents a significant advance over MALDI in terms of specificity, selectivity and sensitivity. In MALDI, the analyte solution is mixed with a matrix solution and the mixture is allowed to crystallize after being deposited on an inert probe surface, trapping the analyte. The matrix is selected to absorb the laser energy and apparently impart it to the analyte, resulting in desorption and ionization. Generally, the matrix absorbs in the UV range. MALDI for large proteins is described in, e.g., U.S. Pat. No. 5,118,937 (Hillenkamp et al.) and U.S. Pat. No. 5,045,694 (Beavis and Chait).

SELDI is described in U.S. Pat. No. 5,719,060 (Hutchens and Yip). SELDI is a method for desorption in which the analyte is presented to the energy stream on a surface that captures the analyte and, thereby, enhances analyte capture and/or desorption.

One version of SELDI, called SEAC (Surface-Enhanced Affinity Capture), involves presenting the analyte to the desorbing energy in association with an affinity capture device (i.e., an adsorbent) attached to probe surface. When an analyte is so adsorbed, the desorbing energy source is provided with a greater opportunity to desorb the target analyte. An energy absorbing material, e.g., matrix, usually is added to the probe to aid desorption of biomolecules, prior to presenting the probe to the energy source, e.g., laser, for desorbing the analyte. Typically used matrix materials include sinapinic acid (SPA) and alpha-cyano-4hydroxy cinnamic acid (CHCA).

Another version of SELDI, called SEND (Surface-Enhanced Neat Desorption), uses a layer of energy absorbing material onto which the analyte is placed. A substrate surface comprises a layer of energy absorbing molecules chemically bond to the surface and/or essentially free of crystals. Analyte is then applied alone (i.e., neat) to the surface of the layer, without being substantially mixed with it. The energy absorbing molecules absorb the desorbing energy and cause the analyte to be desorbed. Using SEND, analytes are presented to the energy source in a simple and homogeneous manner, eliminating solution mixtures and random crystallization. SEND provides uniform and predictable results that enable automation of the process. The energy absorbing material can be classical matrix material or can be matrix material whose pH has been neutralized or brought into the basic range. The energy absorbing molecules can be bound to the probe through covalent or noncovalent means.

Another version of SELDI, called SEPAR (Surface-Enhanced Photolabile Attachment and Release) uses photolabile attachment molecules. A photolabile attachment molecule is a divalent molecule having one site covalently bound to a solid phase, such as a flat probe surface, a bead, etc., that is part of the probe. The second site is covalently bound with the affinity reagent or analyte. The photolabile attachment molecule, when bound to both the surface and the analyte, also contains a photolabile bond that can release the affinity reagent or analyte upon exposure to light. The photolabile bond can be within the attachment molecule or at the site of attachment to either the analyte (or affinity reagent) or the probe surface.

The desorbed analyte can be detected by any of several means. When the analyte is ionized in the process of desorption, such as in laser desorption/ionization mass spectrometry, the detector can be an ion detector. Mass spectrometers generally include means for determining the time-of-flight of desorbed ions. This information is converted to mass. One need not determine the mass of desorbed ions, however, to resolve and detect them: the fact that ionized analytes strike the detector at different times provides detection and resolution of them.

A plurality of detection means can be implemented in series to fully interrogate the analyte components and function associated with retentate at each location in the array.

Desorption detectors comprise means for desorbing the analyte from the adsorbent and means for directly detecting the desorbed analyte. That is, the desorption detector detects desorbed analyte without an intermediate step of capturing the analyte in another solid phase and subjecting it to subsequent analysis. Detection of an analyte normally will involve detection of signal strength. This, in turn, reflects the quantity of analyte adsorbed to the adsorbent.

The desorption detector also can include other elements, e.g., a means to accelerate the desorbed analyte toward the detector, and a means for determining the time-of-flight of the analyte from desorption to detection by the detector.

A preferred desorption detector is a laser desorption/ionization mass spectrometer, which is well known in the art. The mass spectrometer includes a port into which the substrate that carries the adsorbed analytes, e.g., a probe, is inserted. Striking the analyte with energy, such as laser energy desorbs the analyte. Striking the analyte with the laser results in desorption of the intact analyte into the flight tube and its ionization. The flight tube generally defines a vacuum space. Electrified plates in a portion of the vacuum tube create an electrical potential which accelerate the ionized analyte toward the detector. A clock measures the time of flight and the system electronics determines velocity of the analyte and converts this to mass. As any person skilled in the art understands, any of these elements can be combined with other elements described herein in the assembly of desorption detectors that employ various means of desorption, acceleration, detection, measurement of time, etc. An exemplary detector further includes a means for translating the surface so that any spot on the array is brought into line with the laser beam.

Informatics

As high-resolution, high-sensitivity datasets acquired using the methods of the invention become available to the art, significant progress in the areas of diagnostics, therapeutics, drug development, biosensor development, and other related areas will occur. For example, disease markers can be identified and utilized for better confirmation of a disease condition or stage (see, U.S. Pat. Nos. 5,672,480; 5,599,677; 5,939,533; and 5,710,007). Subcellular toxicological information can be generated to better direct drug structure and activity correlation (see, Anderson, L., "Pharmaceutical Proteomics: Targets, Mechanism, and Function," paper presented at the IBC Proteomics conference, Coronado, Calif. (Jun. 11-12, 1998)). Subcellular toxicological information can also be utilized in a biological sensor device to predict the likely toxicological effect of chemical exposures and likely tolerable exposure thresholds (see, U.S. Pat. No. 5,811,231). Similar advantages accrue from datasets relevant to other biomolecules and bioactive agents (e.g., nucleic acids, saccharides, lipids, drugs, and the like).

Thus, in another preferred embodiment, the present invention provides a database that includes at least one set of data assay data. The data contained in the database is acquired using a method of the invention and/or a QD-labeled species of the invention either singly or in a library format. The database can be in substantially any form in which data can be maintained and transmitted, but is preferably an electronic database. The electronic database of the invention can be maintained on any electronic device allowing for the storage of and access to the database, such as a personal computer, but is preferably distributed on a wide area network, such as the World Wide Web.

The focus of the present section on databases, which include peptide sequence specificity data is for clarity of illustration only. It will be apparent to those of skill in the art that similar databases can be assembled for any assay data acquired using an assay of the invention.

The compositions and methods described herein for identifying and/or quantitating the relative and/or absolute abundance of a variety of molecular and macromolecular species from a biological sample provide an abundance of information, which can be correlated with pathological conditions, predisposition to disease, drug testing, therapeutic monitoring, gene-disease causal linkages, identification of correlates of immunity and physiological status, among others. Although the data generated from the assays of the invention is suited for manual review and analysis, in a preferred embodiment, prior data processing using high-speed computers is utilized.

An array of methods for indexing and retrieving biomolecular information is known in the art. For example, U.S. Pat. Nos. 6,023,659 and 5,966,712 disclose a relational database system for storing biomolecular sequence information in a manner that allows sequences to be catalogued and searched according to one or more protein function hierarchies. U.S. Pat. No. 5,953,727 discloses a relational database having sequence records containing information in a format that allows a collection of partial-length DNA sequences to be catalogued and searched according to association with one or more sequencing projects for obtaining full-length sequences from the collection of partial length sequences. U.S. Pat. No. 5,706,498 discloses a gene database retrieval system for making a retrieval of a gene sequence similar to a sequence data item in a gene database based on the degree of similarity between a key sequence and a target sequence. U.S. Pat. No. 5,538,897 discloses a method using mass spectroscopy fragmentation patterns of peptides to identify amino acid sequences in computer databases by comparison of predicted mass spectra with experimentally-derived mass spectra using a closeness-of-fit measure. U.S. Pat. No. 5,926,818 discloses a multidimensional database comprising a functionality for multi-dimensional data analysis described as on-line analytical processing (OLAP), which entails the consolidation of projected and actual data according to more than one consolidation path or dimension. U.S. Pat. No. 5,295,261 reports a hybrid database structure in which the fields of each database record are divided into two classes, navigational and informational data, with navigational fields stored in a hierarchical topological map which can be viewed as a tree structure or as the merger of two or more such tree structures.

The present invention provides a computer database comprising a computer and software for storing in computer-retrievable form assay data records cross-tabulated, for example, with data specifying the source of the target-containing sample from which each sequence specificity record was obtained.

In an exemplary embodiment, at least one of the sources of target-containing sample is from a tissue sample known to be free of pathological disorders. In a variation, at least one of the sources is a known pathological tissue specimen, for example, a neoplastic lesion or a tissue specimen containing a pathogen such as a virus, bacteria or the like. In another variation, the assay records cross-tabulate one or more of the following parameters for each target species in a sample: (1) a unique identification code, which can include, for example, a target molecular structure and/or characteristic separation coordinate (e.g., electrophoretic coordinates); (2) sample source; and (3) absolute and/or relative quantity of the target species present in the sample.

The invention also provides for the storage and retrieval of a collection of target data in a computer data storage apparatus, which can include magnetic disks, optical disks, magneto-optical disks, DRAM, SRAM, SGRAM, SDRAM, RDRAM, DDR RAM, magnetic bubble memory devices, and other data storage devices, including CPU registers and on-CPU data storage arrays. Typically, the target data records are stored as a bit pattern in an array of magnetic domains on a magnetizable medium or as an array of charge states or transistor gate states, such as an array of cells in a DRAM device (e.g., each cell comprised of a transistor and a charge storage area, which may be on the transistor). In one embodiment, the invention provides such storage devices, and computer systems built therewith, comprising a bit pattern encoding a protein expression fingerprint record comprising unique identifiers for at least 10 target data records cross-tabulated with target source.

When the target is a peptide or nucleic acid, the invention preferably provides a method for identifying related peptide or nucleic acid sequences, comprising performing a computerized comparison between a peptide or nucleic acid sequence assay record stored in or retrieved from a computer storage device or database and at least one other sequence. The comparison can include a sequence analysis or comparison algorithm or computer program embodiment thereof (e.g., FASTA, TFASTA, GAP, BESTFIT) and/or the comparison may be of the relative amount of a peptide or nucleic acid sequence in a pool of sequences determined from a polypeptide or nucleic acid sample of a specimen.

The invention also preferably provides a magnetic disk, such as an IBM-compatible (DOS, Windows, Windows95/98/2000, Windows NT, OS/2) or other format (e.g., Linux, SunOS, Solaris, AIX, SCO Unix, VMS, MV, Macintosh, etc.) floppy diskette or hard (fixed, Winchester) disk drive, comprising a bit pattern encoding data from an assay of the invention in a file format suitable for retrieval and processing in a computerized sequence analysis, comparison, or relative quantitation method.

The invention also provides a network, comprising a plurality of computing devices linked via a data link, such as an Ethernet cable (coax or 10BaseT), telephone line, ISDN line, wireless network, optical fiber, or other suitable signal transmission medium, whereby at least one network device (e.g., computer, disk array, etc.) comprises a pattern of magnetic domains (e.g., magnetic disk) and/or charge domains (e.g., an array of DRAM cells) composing a bit pattern encoding data acquired from an assay of the invention.

The invention also provides a method for transmitting assay data that includes generating an electronic signal on an electronic communications device, such as a modem, ISDN terminal adapter, DSL, cable modem, ATM switch, or the like, wherein the signal includes (in native or encrypted format) a bit pattern encoding data from an assay or a database comprising a plurality of assay results obtained by the method of the invention.

In a preferred embodiment, the invention provides a computer system for comparing a query target to a database containing an array of data structures, such as an assay result obtained by the method of the invention, and ranking database targets based on the degree of identity and gap weight to the target data. A central processor is preferably initialized to load and execute the computer program for alignment and/or comparison of the assay results. Data for a query target is entered into the central processor via an I/O device. Execution of the computer program results in the central processor retrieving the assay data from the data file, which comprises a binary description of an assay result.

The target data or record and the computer program can be transferred to secondary memory, which is typically random access memory (e.g., DRAM, SRAM, SGRAM, or SDRAM). Targets are ranked according to the degree of correspondence between a selected assay characteristic (e.g., binding to a selected binding functionality) and the same characteristic of the query target and results are output via an I/O device. For example, a central processor can be a conventional computer (e.g., Intel Pentium, PowerPC, Alpha, PA-8000, SPARC, MIPS 4400, MIPS 10000, VAX, etc.); a program can be a commercial or public domain molecular biology software package (e.g., UWGCG Sequence Analysis Software, Darwin); a data file can be an optical or magnetic disk, a data server, a memory device (e.g., DRAM, SRAM, SGRAM, SDRAM, EPROM, bubble memory, flash memory, etc.); an I/O device can be a terminal comprising a video display and a keyboard, a modem, an ISDN terminal adapter, an Ethernet port, a punched card reader, a magnetic strip reader, or other suitable I/O device.

The invention also preferably provides the use of a computer system, such as that described above, which comprises: (1) a computer; (2) a stored bit pattern encoding a collection of peptide sequence specificity records obtained by the methods of the invention, which may be stored in the computer; (3) a comparison target, such as a query target; and (4) a program for alignment and comparison, typically with rank-ordering of comparison results on the basis of computed similarity values.

EXAMPLES

Example 1

The following protocol describes a manual procedure to prepare latex based adsorbent biochips bearing strong anion exchange (SAX), weak anion exchange (WAX), strong cation exchange (SCX), weak anion exchange (WAX) and immobilized metal chelate (IMAC) binding functionalities.

The following protocol describes a manual procedure to prepare latex based adsorbent biochips bearing strong anion exchange (SAX), weak anion exchange (WAX), strong cation exchange (SCX), weak anion exchange (WAX) and immobilized metal chelate (IMAC) binding functionalities.

1.1. Preparation of Poly-Vinylbenzylchloride Latex (600 g Batch)

- a) Combine in a 1 L, narrow-mouth glass bottle:
  - 0.57 g ammonium persulfate (99.99% purity Aldrich Chemical Co., Milwaukee, Wis.);
  - 560 mL water; and
  - 4.79 g of 11.91% stock solution of sodium dihexyl sulfosuccinate in isopropanol and water (Aerosol® MA 80 surfactant Cytec Industries, East Patterson N.J.);
- b) magnetically stir, purging continuously with argon for 60 min;
- c) add while stirring:
  - 30 g pure para isomer vinylbenzyl chloride (Aldrich catalog no. 43,688-7); and
  - 4.75 g of 10% solution of sodium metabisulfate;
- d) remove stir bar, cap bottle, agitate in warm air bath (350 orbits/min for 15 min, then 250 orbits/min for 26 hrs at 31° C.;
- e) rinse mixed bed ion exchange resin (Bio-Rad® AG 501-X8) with purest deionized water. Add 18-19 g of resin to mixture;
- f) agitate gently at about 4° C. for about 2 days;
- g) store at 4° C. (mixed bed resin can be removed by filtering through loose glass wool).

1.2 Functionalization of Poly Vinylbenzylchloride Latex 1.2a Strong Anion Exchange Latex Bead Functionalization

- a) Combine while stirring:
  - raw latex beads from Example 1.1 (150 g);
  - 0.25 M N,N-dimethyloctylamine in 1% Triton X-100 (75g) (Aldrich, catalog no. 25,622-6); and
  - 0.1 M tetramethyl-1,4-butanediamine (60g); (Aldrich, catalog no. 12,710-8);

b) stir in 1 liter narrow mouth bottle for 24 hours at 37° C.;

c) add 0.25 M N,N-dimethyloctylamine in 1% Triton X-100 (225 g);

d) stir again for 24 hours at 37° C.;

e) centrifuge and wash functionalized latex beads with deionized water, 1M sodium hydroxide and then with deionized water until supernatant pH is between 7-8.

1.2b Weak Anion Exchange Latex Bead Functionalization a) Combine while stirring:

raw latex beads from Example 1.1 (150g);

0.25M dimethyl sulfide in 1% Triton X-100 (300g, Aldrich, catalog no. 45,157-7);

0.1M tetramethyl-1,4-butanediamine (10g, Aldrich, catalog no. 12,710-8).

b) stir in 1L flask with 3 neck angles closed with stoppers for 24 hours at 35° C. in a ventilated hood;

c) add 1.5 M N-Methyl-d-glutamine (300g, Fluka, catalog no. 66930);

d) Continue to stir in 1L flask with 3 neck angles, 2 closed with stoppers and one closed with a simple condenser to let out the dimethyl sulfide gas without losing any water for 24 hours at 70° C. in a ventilated hood;

e) Centrifuge and wash functionalized latex beads with deionized water, 1M sodium hydroxide and then with deionized water until supernatant pH is between 7-8.

1.2c Strong Cation Exchange Latex Functionalization a) Combine while stirring:

raw latex beads from Example 1.1 (150 g);

0.25M Dimethyl sulfide in 1% Triton X-100 (300g, Aldrich, catalog no. 45,157-7);

0.1M tetramethyl-1,4-butanediamine (10g, Aldrich, catalog no. 12,710-8)

b) stir in 1L flask with 3 neck angles closed with stoppers for 24 hours at 35° C. in a ventilated hood;

c) add 1M 3-mercapto-1-propanesulfonic acid (300 g, Aldrich, catalog no. 25168-2);

d) continue to stir in 1L flask with 3 neck angles, 2 closed with stoppers and one closed with a simple condenser to let out the dimethyl sulfide gas without loosing any water for 24 hours at 70° C. in a ventilated hood;

e) centrifuge and wash functionalized latex beads with deionized water, 1M sodium hydroxide, 0.25M acetic acid and then with deionized water until supernatant pH is between 5-6.

1.2d Weak Cation Exchange Latex Functionalization a) Combine while stirring:

raw latex beads from Example 1.1 (150 g);

0.25 M dimethyl sulfide in 1% Triton X-100 (300g, Aldrich, catalog no. 45,157-7);

0.1M Tetramethyl-1,4-butanediamine (10g, Aldrich, catalog no. 12,710-8);

b) stir in 1L flask with 3 neck angles closed with stoppers for 24 hours at 35° C. in a ventilated hood;

c) add 1M of 3-mercaptopropionic acid (300 g, Aldrich, catalog no. M580-1);

d) continue to stir in 1L flask with 3 neck angles, 2 closed with stoppers and one closed with a simple condenser to let out the dimethyl sulfide gas without loosing any water for 24 hours at 70° C. in a ventilated hood;

e) centrifuge and wash functionalized latex beads with deionized water, 1M sodium hydroxide, 0.25M acetic acid and then with deionized water until supernatant pH is between 5-6.

1.2e Immobilized Metal Chelate Latex Functionalization a) Combine while stirring:

raw latex beads from Example 1.1 (150 g);

0.25M dimethyl sulfide in 1% Triton X-100 (300g, Aldrich, catalog no. 45,157-7);

0.1M tetramethyl-1,4-butanediamine (10 g, Aldrich, catalog no. 12,710-8);

b) stir in 1L flask with 3 neck angles closed with stoppers for 24 hours at 35° C. in a ventilated hood;

c) Add 1M of N,N-bis(carboxymethyl)-L-lysine hydrate (300 g, Fluka, catalog no. 14580);

d) continue to stir in 1 liter flask with 3 neck angles, 2 closed with stoppers and one closed with a simple condenser to let out the dimethyl sulfide gas without loosing any water for 24 hours at 70° C. in a ventilated hood;

e) Centrifuge and wash functionalized latex beads with deionized water, 1M sodium hydroxide, 0.25M acetic acid and then with deionized water until supernatant pH is between 5-6.

1.3 Substrate

The substrate is a flat aluminum (6463-T6) blank having dimensions 9 mm×78 mm. The surface is derivatized with silicon dioxide by sputtering.

Addressable locations ("spots") are created on the substrate surface by coating with a perfluorinated polymer, leaving "holes" in the coating to define the spots.

1.4 Silane Coupling Reaction a) Preparation of silane solution:

0.2 mM acetic Acid (2.0g);

3-(trimethoxysilyl)propylmethacrylate (0.80g, Aldrich Chemical, catalog no. 44015-9);

methanol (30.0g);

let the solution react for 10 minutes at room temperature;

b) immerse chip in the silane solution (e.g., insert chip in ~8 mL tube and fill with solution from step a) and let it react for 10 minutes on a tumbler;

c) wash the chip with acetone and then with water;

d) after derivatization and cleaning the chip, cure it at 100°-110° C. for 10 minutes.

Note: Up to this step, i.e., Example 1.4, all the chips can be prepared together. In the next steps, they may be separated depending upon the type of latex loaded on the surface.

1.5 Attaching the Brush Polymers 1.5a: Negatively Charged Polymers for the Anion Exchange Protein Chip (SAX and WAX)

a) prepare the photo-initiator solution by dissolving 0.1 g of 2-hydroxy-4-(2hydroxyethoxy)-2-methyl-propiophenone (Aldrich, catalog no. 41089-6) in 20 g of deionized water, and heating the solution in the microwave oven for 10 seconds (at this scale) to dissolve the initiator in water;

b) preparation of monomer-initiator solution:

combine the monomer and the initiator in a one to ten ratio-acrylic acid monomer (0.5 g, Aldrich, catalog no. 14723-0);

initiator solution, from step (a), (5.0g);

c) load 2 μL of the monomer-initiator solution on the each spot ("addressable location") of the substrate prepared in Example 1.4;

d) after loading the monomer-initiator solution on the chip, process it under the UV lamp for 10 minutes;

e) wash the chip with deionized water and then dry the surface, preparing the chip for the addition of anion exchange latex.

1.5b Positively Charged Polymers for the Cation Exchange Protein Biochip (WCX, SCX, IMAC)

a) prepare the photo initiator solution by dissolving 0.1g of 2-hydroxy-4-(2-hydroxyethoxy)-2-methyl propiophenone in 20 g of deionized water, heating the solution in the microwave oven for 10 seconds (at this scale) to dissolve the initiator in the water;

b) preparation of monomer-initiator solution:

prepare the monomer-imitator solution in one to ten ratio;

N-(3,N,N dimethyl amino propyl) methacrylamide monomer (0.5 g, Polyscience, Inc., catalog no. 09-656);

initiator solution (5.0 g);

c) load 2 µL of the monomer-initiator solution on the each spot of the chip prepared in Example 1.2;

d) after loading the monomer-initiator on the chip, process it under the UV lamp for 10 minutes;

e) wash the chip with deionized water and then dry the surface, preparing the chip for the addition of latex functionalized for cation exchange or IMAC.

1.6 Loading Latex on the Biochip 1.6a Anion Exchange Biochip

Load 2-5 µL of anion exchange latex on the chip and then wash it with deionized water, preparing the biochip for use.

1.6b Cation Exchange Biochip

Load 2-5 µL of cation exchange latex on the protein chip and then wash it with deionized water, preparing the biochip for use.

1.6c Immobilized Metal Chelate Biochip a) Load 2-5 µL of IMAC latex on the protein biochip, then wash with deionized water;

b) add 5 µL per spot of a 0.1M $CuSO_4$ solution (or solution of other metal salt such as Ni, Fe, Zn, Ga or Co.), preparing the biochip for use.

Example 2

The following protocol describes a procedure to prepare poly-vinylbenzyl chloride (VBC) latex by a technique known as "seed-growth" or "step-growth." The process includes two-steps: incubating VBC monomer to the latex seed for 15-60 minutes; and polymerization.

2.1 Preparation of Poly-Vinylbenzyl Chloride Latex via Seed-Growth a) Combine in a 1L, narrow-mouth glass bottle:

0.57 g ammonium persulfate (99.99% purity Aldrich Chemical Co., Milwaukee, Wis.);

565 g water;

seed latex (72.6 g, prepared as described in Example 1.1 and filtered through Pyrex product number 3950, glass wool); and 27 g VBC monomer, Dow Chemical, mixed m and p isomer;

b) magnetically stir, purging continuously with argon for 15 min;

c) add, while stirring, 10% solution of sodium metabisulfate (4.75 g);

d) remove stir bar, cap bottle, agitate in warm air bath (305 orbits/min for 29.3 h at 35° C.);

e) thoroughly rinse (with water) mixed-bed, ion exchange resin, AG 501-X8, Bio-Rad (18 g), near the end of the 29.3 h polymerization time;

f) preclean a 1L bottle by rinsing and sonicating with reagent grade ethanol, and thoroughly dry until no residual odor of ethanol remains;

g) add the AG 501-X8 resin and the polymerized VBC to the precleaned 1L bottle;

h) place the bottle on a refrigerated roller mill (7° C.) for at least 18 h.

2.2 Storage and use of Poly-Vinylbenzylchloride Latex a) store the latex at 7° C. (or less, but do not freeze) in contact with the AG 501-X8 (the latex can be stored in this manner for extended periods without apparent change);

b when ready for use, separate the latex from the AG 501-X8 by filtering through a small wad of Pyrex wool, Corning Product No. 3950, just prior to using for further reaction or chemical tests.

The present invention provides a novel adsorbent biochip, methods of use and manufacture. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted. By their citation of various references in this document, Applicants do not admit any particular reference is "prior art" to their invention.

What is claimed is:

1. A method of detecting an analyte, said method comprising:

(a) contacting said analyte with a chip comprising:

(i) a planar substrate comprising a surface;

(ii) an intermediate layer covalently attached to said surface, wherein said intermediate layer comprises charged linker arms; and (iii) an adsorbent film attached to said intermediate layer by an electrostatic interaction, said adsorbent film comprising a plurality of charged latex particles bound to said linker arms wherein each said charged latex particle has a diameter of about 3 microns to about 500 microns, and wherein each said charged latex particle comprises a binding functionality wherein said binding functionality interacts with said analyte, thereby adsorbing said analyte on said adsorbent film, and wherein said charged linker arms and said charged latex particles are oppositely charged; and (b) desorbing said analyte and detecting said desorbed analyte using mass spectrometry.

2. The method according to claim 1, wherein said surface comprises at least one addressable feature, said addressable feature having said intermediate layer attached thereto and said intermediate layer having said adsorbent film attached thereto.

3. The method according to claim 1, wherein said binding functionality is selected from the group consisting of positively charged functinctionalities, negatively charged functionalities, metal ion functionalities, polar functionalities, hydrophobic functionalities and combinations thereof.

4. The method according to claim 1, wherein said binding functionality comprises a biomolecule.

5. The method according to claim 1, wherein said particles are from about 3 microns to about 10 microns in diameter.

6. The method according to claim 1, wherein said particles are from about 10 microns to about 500 microns in diameter.

7. The method according to claim 1, wherein the analyte is detected by laser desorption/ionization mass spectrometry.

8. The method according to claim 7, said method further comprising:

(c) prior to step (b), washing said chip, thereby removing analyte not interacting with a binding functionality.

9. The method according to claim 1, said chip comprising:

(i) an aluminum substrate comprising a silicon dioxide surface;

(ii) an intermediate layer attached to said surface, said intermediate layer comprising a moiety having the formula:

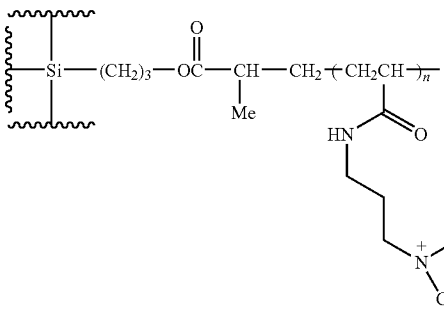

wherein n is an integer greater than 1; and (iii) an adsorbent film immobilized electrostatically on said intermediate layer, said adsorbent film comprising a plurality of adsorbent particles comprising the subunit:

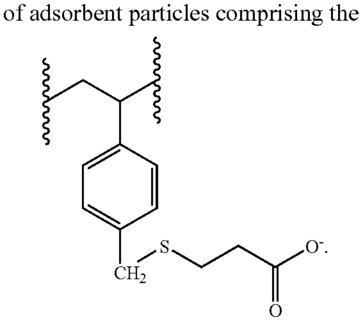

10. The method according to claim 1, said chip comprising:

(i) said substrate is an aluminum substrate comprising a silicon dioxide surface;

(ii) said intermediate layer comprises a polymer formed by co-polymerization of acrylic acid and a propylmethacrylate moiety immobilized on said silicon dioxide surface through a Si—O—Si bond; and (iii) said adsorbent film comprises a plurality of charged latex particles comprising the subunit:

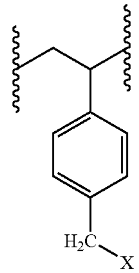

wherein

X is a member selected from:

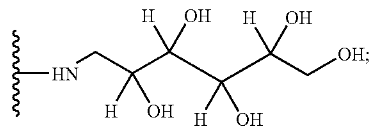

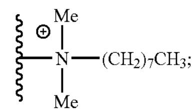

and

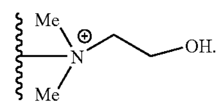

11. The method according to claim 10, said intermediate layer comprising a moiety having the formula:

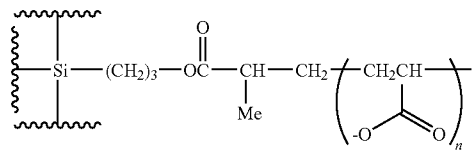

wherein n is an integer greater than 1.

12. The method according to claim 1, said chip comprising:

(i) an aluminum substrate comprising a silicon dioxide surface;

(ii) an intermediate layer attached to said surface, said intermediate layer comprising a polymer formed by co-polymerization of N-(3-N,N-dimethylaminopropyl) methacrylamide and a propylmethacrylate moiety immobilized on said surface through a Si—O—Si bond; and (iii) an adsorbent film immobilized electrostatically on said intermediate layer, said adsorbent film comprising a plurality of adsorbent particles comprising the subunit:

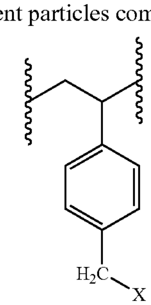

wherein

X is a member selected from:

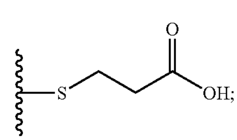

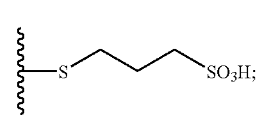

and

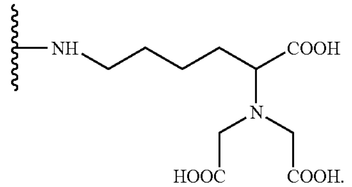

13. The method according to claim 12, said intermediate layer comprising a moiety having the formula:

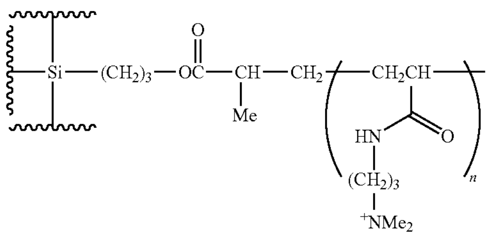

wherein n is an integer greater than 1.

14. The method according to claim 1, wherein (i) said substrate is an aluminum substrate comprises a silicon dioxide surface;

(ii) said intermediate layer comprises a moiety having the formula:

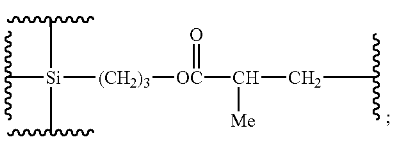

and (iii) said adsorbent particles comprise the subunit:

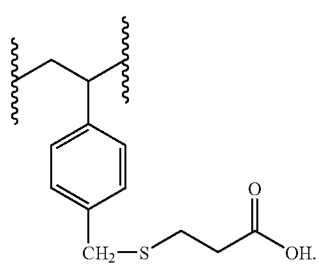

15. The method according to claim 1, wherein (i) said substrate is an aluminum substrate comprising a silicon dioxide surface;

(ii) said intermediate layer comprises a moiety having the formula:

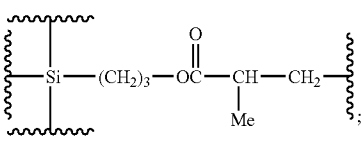

and (iii) said adsorbent particles comprise the subunit:

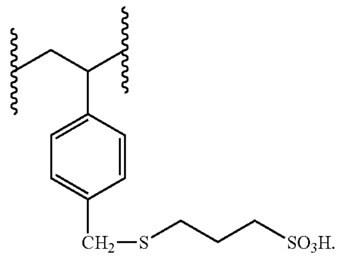

16. The method according to claim 1, wherein (i) said substrate is an aluminum substrate comprising a silicon dioxide surface;

(ii) said intermediate layer comprises a moiety having the formula:

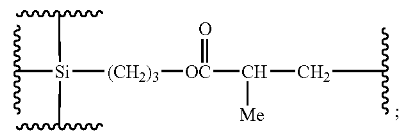

and (iii) said adsorbent particles comprise the subunit:

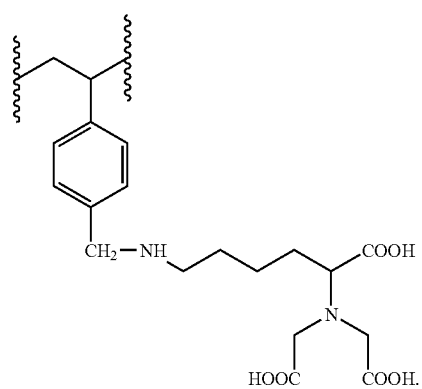

17. A method of detecting an analyte, said method comprising (a) contacting said analyte with a chip comprising:

(i) an aluminum substrate comprising a silicon dioxide surface;

(ii) an intermediate layer comprising a moiety having the formula:

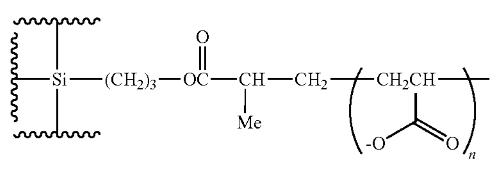

wherein n is an integer greater than 1; and (iii) an adsorbent film attached to said intermediate layer by an electrostatic interaction, said adsorbent film comprising a plurality of charged latex particles comprising the subunit:

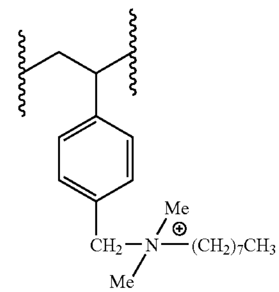

wherein each said latex particle as a diameter from about 3 microns to about 500 microns; and (b) desorbing said analyte and detecting said desorbed analyte using mass spectrometry.

18. A method of detecting an analyte, said method comprising:

(a) contacting said analyte with a chip comprising:

(i) a planar substrate comprising a surface;

(ii) an intermediate layer covalently attached to said surface, wherein said intermediate layer comprises charged linker arms; and (iii) an adsorbent film attached to said intermediate layer by an electrostatic interaction, said adsorbent film comprising a plurality of charged latex particles bound to said linker arms, wherein said charged latex particles comprise a subunit which is a member selected from:

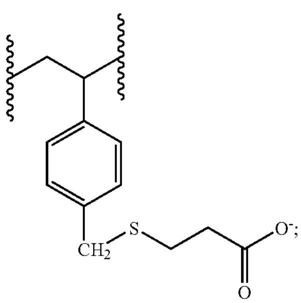

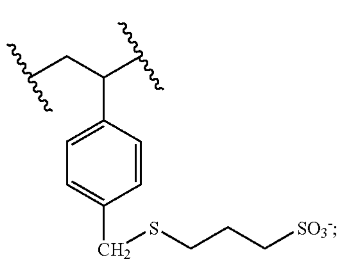

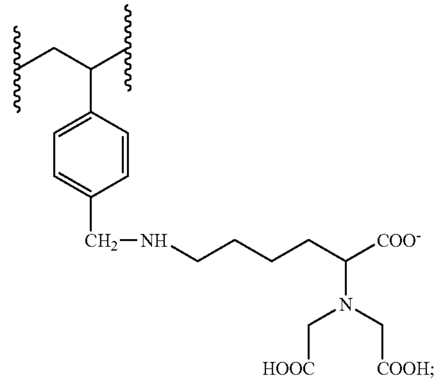

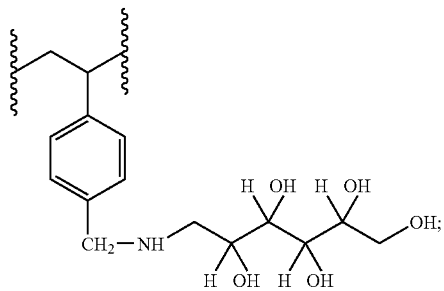

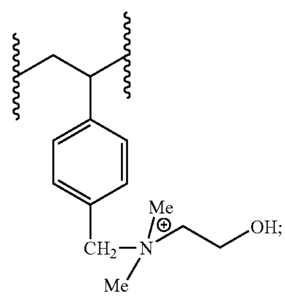

and

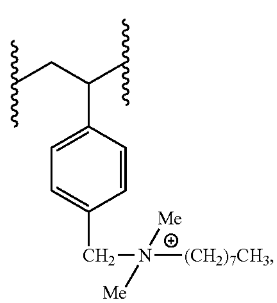

wherein each said charged latex particle has a diameter of from about 3 microns to about 500 microns, wherein each said charged latex particle comprises a binding functionality wherein said binding functionality interacts with said analyte, thereby adsorbing said analyte on said adsorbent film, and wherein said charged linker arms and said charged latex particles are oppositely charged; and (b) desorbing said analyte and detecting said desorbed analyte using mass spectrometry.

19. A method of detecting an analyte, said method comprising:

(a) contacting said analyte with a chip comprising:

(i) an aluminum substrate comprising a silicon dioxide surface;

(ii) an intermediate layer covalently attached to said surface, wherein said intermediate layer comprises charged linker arms; and (iii) an adsorbent film attached to said intermediate layer by an electrostatic interaction, said adsorbent film comprising a plurality of charged latex particles bound to said linker arms, wherein each said charged particle has a diameter of from about 3 microns to about 500 microns, wherein each said charged latex particle comprises a binding functionality wherein said binding functionality interacts with said analyte, thereby adsorbing said analyte on said adsorbent film, and wherein said charged linker arms and said charged latex particles are oppositely charged; and (b) desorbing said analyte and detecting said desorbed analyte using mass spectrometry.

* * * * *